US005639751A

United States Patent [19]
Andrási et al.

[11] Patent Number: 5,639,751
[45] Date of Patent: *Jun. 17, 1997

[54] N-ACYL-2,3-BENZODIAZEPINE DERIVATIVES FOR TREATING ACUTE AND CHRONIC NEURODEGENERATIVE DISORDERS

[75] Inventors: Ferenc Andrási; Pál Berzsenyi; Péter Botka; Sándor Farkas; Katalin Goldschmidt; Tamás Hámori; Jenő Kőrösi; Imre Moravcsik; István Tarnawa, all of Budapest, Hungary

[73] Assignee: Cyogyszerkutato Intezet KFT, Budapest, Hungary

[*] Notice: The term of this patent shall not extend beyond the expiration date of Pat. No. 5,519,019.

[21] Appl. No.: 477,801

[22] Filed: Jun. 7, 1995

Related U.S. Application Data

[60] Continuation-in-part of Ser. No. 423,152, Apr. 17, 1995, abandoned, which is a division of Ser. No. 80,604, Jun. 21, 1993, Pat. No. 5,459,137, which is a continuation-in-part of Ser. No. 48,347, Apr. 15, 1993, abandoned, which is a continuation-in-part of Ser. No. 809,361, Dec. 17, 1991, abandoned.

[30] Foreign Application Priority Data

Dec. 21, 1990 [HU] Hungary ................... 8398/90

[51] Int. Cl.$^6$ .................. A61K 31/55; A61K 31/44
[52] U.S. Cl. .................. 514/220; 514/221; 514/468
[58] Field of Search .................. 514/220, 221, 514/468

[56] References Cited

U.S. PATENT DOCUMENTS

| | | | |
|---|---|---|---|
| 4,614,740 | 9/1986 | Láng et al. | 514/221 |
| 4,835,152 | 5/1989 | Kőrösi et al. | 514/220 |
| 5,459,137 | 10/1995 | Andrási et al. | 514/220 |
| 5,519,019 | 5/1996 | Andrási et al. | 514/220 |
| 5,521,174 | 5/1996 | Andrási et al. | 514/220 |

*Primary Examiner*—Kevin E. Weddington
*Attorney, Agent, or Firm*—Keil & Weinkauf

[57] ABSTRACT

The invention relates to novel N-acyl-2,3-benzodiezapine derivatives of the general formula (I), their stereoisomers and acid-addition salts, pharmaceutical compositions containing them and a process for their preparation. In the general formula (I)

R stands for a $C_{1-6}$ alkanoyl group optionally substituted by a methoxy, cyano, carboxyl, amino, $C_{1-4}$ alkylamino, di($C_{1-4}$ alkyl)amino, pyrrolidino, phthalimido or phenyl group, or by one or more halogen(s); or R is a benzoyl, cyclopropanecarbonyl, $C_{1-5}$ alkylcarbamoyl or phenylcarbamoyl group; or R is absent when a double bond exists between the N(3) and C(4) atoms;

$R^1$ means hydrogen; or $R^1$ is absent when a double bond exists between the N(3) and C(4) atoms;

$R^2$ means a $C_{1-3}$ alkyl group; or $R^1$ and $R^2$ together stand for a methylene group and no double bond is present between the N(3) and C(4) atoms;

$R^3$ means hydrogen or a $C_{1-4}$ alkanoyl group;

$R^4$ represents hydrogen; a $C_{1-6}$ alkanoyl group optionally substituted by a methoxy, cyano, carboxyl, amino, $C_{1-4}$ alkylamino, di($C_{1-4}$ alkyl)amino, pyrrolidino, phthalimido or phenyl group or by one or more halogen(s); as well as a benzoyl, palmitoyl, cyclopropanecarbonyl, $C_{1-5}$ alkylcarbamoyl or phenylcarbamoyl group; and the dotted lines represent valence bonds optionally being present, with the proviso that no double bond exists between the N(3) and C(4) atoms when both $R^3$ and $R^4$ stand for hydrogen.

The compounds of the general formula (I) possess valuable central nervous system effects, particularly muscle-relaxant, anticonvulsive and neuroprotective action. Thus, they may be useful for the treatment of various diseases of central nervous system origin.

6 Claims, No Drawings

N-ACYL-2,3-BENZODIAZEPINE DERIVATIVES FOR TREATING ACUTE AND CHRONIC NEURODEGENERATIVE DISORDERS

CROSS-REFERENCE

This application is a continuation-in-part of copending U.S. application Ser. No. 08/423,152, filed Apr. 17, 1995 now abandoned which is a divisional application of U.S. application Ser. No. 08/080,604, filed June 21, 1993 now U.S. Pat. No. 5,459,137 which is a continuation-in-part of abandoned U.S. application Ser. No. 08/048,347, filed Apr. 15, 1993, which is a continuation-in-part of abandoned U.S. application Ser. No. 07/809,361, filed Dec. 17, 1991.

Description

This invention relates to novel N-acyl-2,3-benzodiazepine derivatives of the formula (I)

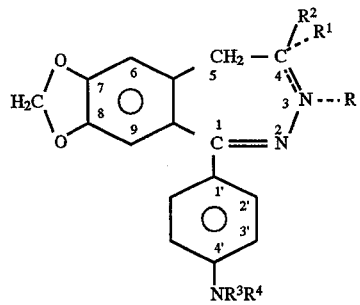

wherein

R is a $C_{1-6}$alkanoyl group optionally substituted by a methoxy, cyano, carboxyl, amino, $C_{1-4}$alkylamino, di($C_{1-4}$alkyl)amino, pyrrolidino, phthalimido or phenyl group, or by one or more halogen(s); or R is a benzoyl, cyclopropanecarbonyl, $C_{1-5}$alkylcarbamoyl or phenylcarbamoyl group; or R is absent when a double bond exists between the N(3) and C(4) atoms;

$R^1$ is hydrogen; or $R^1$ is absent when a double bond exists between the N(3) and C(4) atoms;

$R^2$ is a $C_{1-3}$alkyl group; or $R^1$ and $R^2$ together form a methylene group;

$R^3$ is hydrogen or a $C_{1-4}$alkanoyl group;

$R^4$ is hydrogen; a $C_{1-6}$alkanoyl group optionally substituted by a methoxy, cyano, carboxyl, amino, $C_{1-4}$alkylamino, di($C_{1-4}$alkyl)amino, pyrrolidino, phthalimido or phenyl group or by one or more halogen (s); as well as a benzoyl, palmitoyl, cyclopropanecarbonyl, $C_{1-5}$alkylcarbamoyl or phenylcarbamoyl group;

the dotted lines represent valence bonds optionally being present, with the proviso that no double bond exists between the N(3) and C(4) atoms when both $R^3$ and $R^4$ stand for hydrogen;

stereoisomers of said compounds and acid-addition salts of said compounds.

The compounds of the formula (I) according to the invention have an asymmetric molecular structure. The formula (I) relates to all possible individual stereoisomers and their mixtures.

The invention also provides compounds which are useful in the preparation of N-acyl-2,3-benzodiazepine derivatives.

A further aspect of the present invention relates to novel intermediate compounds of the formula (V):

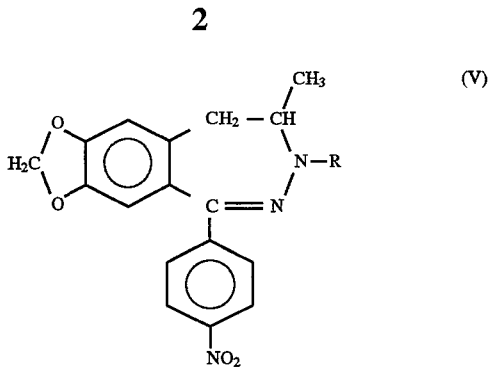

wherein

R is hydrogen; a $C_{1-6}$alkanoyl group optionally substituted by a methoxy, cyano, carboxyl, amino, $C_{1-4}$alkylamino, di($C_{1-4}$alkyl)amino, pyrrolidino, phthalimido or phenyl group, or by one or more halogens(s); or R is a benzoyl, cyclopropanecarbonyl, $C_{1-5}$alkylcarbamoyl or phenylcarbamoyl group;

and the stereoisomers of said compounds.

Furthermore the invention provides a process for preparing a compound of the formula (V), wherein R is hydrogen;

and stereoisomers of said compound.

According to an other aspect of the invention, there is provided a process for the preparation of the new compounds of the formula (I) and the acid-addition salts thereof.

The new compounds of the formula (I) inhibit the activation of one or more excitatory amino acid receptors and possess valuable central nervous system (CNS), particularly muscle-relaxant, anticonvulsive and/or neuroprotective activity.

Excitatory amino acids, mainly glutamate, are known to be the most important excitatory neurotransmitter substances, which play an essential role in normal physiological processes in the central nervous system of mammals. Excitatory amino acids activate both ionotropic (ligand-gated ionic channels) and metabotropic (G-protein coupled) receptors, using second messenger systems.

According to their sensitivities to different agonists, the ionotropic receptors were originally classified as NMDA, AMPA, and kainate (formerly quisqualate) receptors. Novel molecular biological studies confirmed this classification based on pharmacological sensitivities and revealed that several NMDA, AMPA, and kainate receptor subtypes exist [Ann. Rev. Neurosci. 17, 31 (1994)]. Four different AMPA receptor subunits are known up to now, not including the splice variants. Each functioning AMPA receptor is composed of five subunits (the complex can be either homomer or heteromer), and forms a cation-permeable ionic channel. The ion permeability and pharmacological sensitivity of the channels are determined by the subunit composition. The term AMPA/kainate receptor is sometimes used instead of AMPA receptors as kainate can also activate them. Because of several similarities in their function and drug sensitivity, AMPA and kainate receptors together are also called non-NMDA receptors. Overactivation of any kind of glutamate receptors may lead to pathological processes.

It is generally accepted that AMPA type glutamate receptors play a major role in a variety of central nervous system disorders such as acute and chronic neurodegenerative diseases, epilepsy and muscle spasm. Thus, inhibition of the activation of AMPA receptor results in neuroprotective, antiepileptic and muscle-relaxant effects [Cerebrovasc. Brain Metab. Rev. 6, 225 (1994); Neurology 44 Suppl.8, S14 (1994); J. Pharmacol. Exp. Ther. 260, 742 (1992)].

Inhibition of the activation of AMPA receptors can be achieved by AMPA receptor antagonists of competitive or non-competitive nature. Non-competitive antagonists, in general, may offer definite advantages over competitive ones, as they provide a better protection in situations when the extracellular concentration of excitatory amino acids is extremely high [Epilepsy Res. 15, 179 (1993)].

Beside several competitive AMPA-antagonists, the only non-competitive AMPA-antagonist compound known in the literature is 1-(4-aminophenyl)-4-methyl-7,8-methylene-dioxy-5H-2,3-benzodiazepine (GYKI 52466 U.S. Pat. No. 4,614,740) also invented by the authors of the present invention. GYKI 52466 has been shown to be a highly selective antagonist of AMPA-receptors, with a non-competitive mode of action, i.e. it acts at an allosteric site [Neuron, 10, 51 (1993); ibid. 10, 61 (1993)]. The non-competitive AMPA-antagonist effect, as well as anticonvulsive, muscle-relaxant and neuroprotective activity of GYKI 52466 is well established [TIPS 15, 456 (1994)] by detailed pharmacological studies. However, GYKI 52466 was found to be positive in the AMES test, i.e. it proved to have a mutagenic potential. Thus, it is a specific aim of the present invention to find novel 2,3-benzodiazepine derivatives which retain the valuable pharmacological activity profile of GYKI 52466 but are devoid of its mutagenic potential.

The new compounds of the formula (I), wherein R, $R^1$, $R^2$, $R^3$, $R^4$ and the dotted lines are as defined above and their pharmaceutically acceptable acid-addition salts completely satisfy this requirement.

According to the invention, the compounds of the formula (I) are prepared by a) acylating a compound of the formula (II)

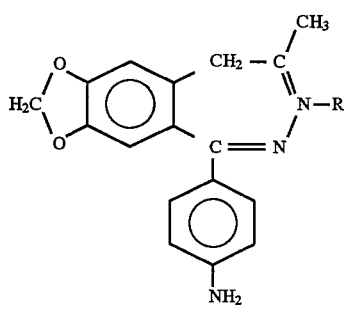

with a $C_{1-6}$alkanoic acid optionally substituted by a methoxy, cyano, carboxyl or phenyl group or by one or more halogen(s); or with benzoic, cyclopropanecarboxylic or palmitic acid or with a reactive derivative thereof; and, if desired, reacting a new compound of the formula (I) thus obtained, wherein $R^4$ is a $C_{1-6}$alkanoyl group substituted by a halogen, with a $C_{1-4}$alkylamine, di($C_{1-4}$alkyl)amine or pyrrolidine, to obtain compounds of the formula (I), wherein $R^2$, $R^3$ and the dotted lines are as defined above, $R^4$ is a $C_{1-6}$alkanoyl group optionally substituted by a methoxy, cyano, carboxyl, phenyl, $C_{1-4}$alkylamino, di($C_{1-4}$alkyl)amino or pyrrolidino group or one or more halogen(s); or a benzoyl, cyclopropanecarbonyl or palmitoyl group; R and $R^1$ are absent and a double bond exists between the N(3) and C(4) atoms;

b) acylating a compound of the formula (III),

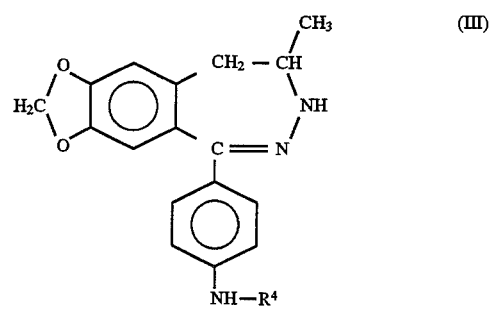

wherein $R^4$ is as defined above, with a $C_{1-6}$alkanoic acid optionally substituted by a methoxy, cyano, carboxyl or phenyl group or by one or more halogen(s); or with benzoic or cyclopropanecarboxylic acid or with a reactive derivative thereof; and, if desired, reacting a new compound of the formula (I) thus obtained, wherein $R^4$ is a $C_{1-6}$alkanoyl group substituted by a halogen, with a $C_{1-4}$alkylamine, di($C_{1-4}$alkyl)amine or pyrrolidine, to obtain compounds of the formula (I), wherein $R^1$, $R^2$, $R^3$, $R^4$ and the dotted lines are as defined above, R is benzoyl or a cyclopropanecarbonyl group, a $C_{1-6}$ alkanoyl group optionally substituted by a methoxy, cyano, carboxyl, phenyl, $C_{1-4}$alkylamino, di($C_{1-4}$alkyl)amino or pyrrolidino group or one or more halogen(s); and no double bond exists between the N(3) and C(4) atoms; or c) acylating a compound of the formula (II) with an N-phthaloylamino acid of the formula (VI),

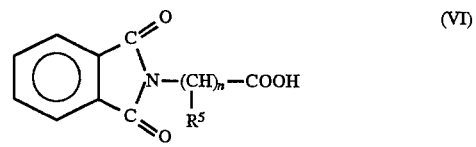

wherein $R^5$ is hydrogen or a $C_{1-4}$alkyl group and n is 1 in case of α-amino acids, whereas $R^5$ is hydrogen and n is an integer of 2 to 5 in case of β-ε-amino acids, and, if desired, removing the phthaloyl group, to obtain compounds of the formula (I), wherein $R^2$ and the dotted lines are as defined above, $R^3$ is hydrogen, $R^4$ is a $C_{1-6}$alkanoyl group substituted by an amino or phthalimido group, both R and $R^1$ are absent, and a double bond is present between the N(3) and C(4) atoms; or d) acylating a compound of the formula (III), wherein $R^4$ is as defined above, with an N-phthaloylamino acid of the formula (VI), wherein $R^5$ is hydrogen or a $C_{1-4}$alkyl group and n is 1 in case of α-amino acids, whereas $R^5$ is hydrogen and n is an integer of 2 to 5 in case of β-ε-amino acids, and, if desired, removing the phthaloyl group, to obtain compounds of the formula (I), wherein $R^1$, $R^2$ and the dotted lines are as defined above, $R^3$ is hydrogen, $R^4$ is as defined above except hydrogen, R is a $C_{1-6}$alkanoyl group substituted by an amino or phthalimido group and no double bond is present between the N(3) and C(4) atoms; or e) reacting a compound of the formula (II) with a $C_{1-5}$alkyl isocyanate or phenyl isocyanate, to obtain compounds of the formula (I), wherein $R^2$ and the dotted lines are as defined above, $R^3$ is hydrogen, $R^4$ is a $C_{1-5}$alkylcarbamoyl or phenylcarbamoyl group, R and $R^1$ are absent and a double bond is present between the N(3) and C(4) atoms; or f) reacting a compound of the formula (III), wherein $R^4$ is defined as above, with a $C_{1-5}$alkyl isocyanate, or phenyl isocyanate, to obtain compounds of the formula (I), Wherein $R^1$, $R^2$ and the dotted lines are as defined above, $R^3$ is hydrogen, $R^4$ is as defined above except hydrogen, R is a $C_{1-5}$ alkylcarbamoyl or phenylcarbamoyl group and no double bond is present between the N(3) and C(4) atoms; or g) selectively reducing a nitro compound of the formula (IV)

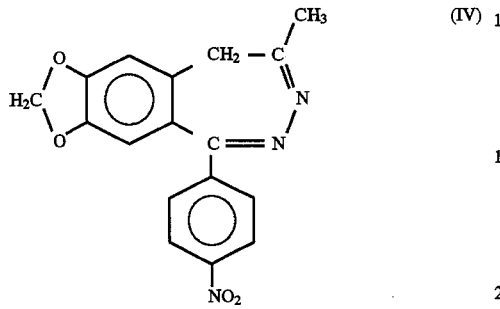

to a novel compound of the formula (V), wherein R is hydrogen, then either acylating the compound of the formula (V) thus obtained by using any of the above processes b), d) or f) and reducing the nitro group of the thus-obtained new compound of the formula (V), wherein R is as defined above, to an amino group, or first reducing the nitro group and then acylating the compound of the formula (III) thus obtained, wherein $R^4$ is hydrogen, by using any of the above processes b), d) or f), to obtain compounds of the formula (I), wherein $R^1$, $R^3$ and $R^4$ are hydrogen, R, $R^2$ and the dotted lines are as defined above and no double bond is present between the N(3) and C(4) atoms; or h) acylating a new compound of the formula (I), wherein R, $R^1$, $R^2$ and the dotted lines are as defined above, $R^3$ and $R^4$ are hydrogen and no double bond is present between the N(3) and C(4) atoms, with a $C_{1-6}$alkanoic acid optionally substituted by a methoxy, cyano or carboxyl group or by one or more halogen(s); or with benzoic acid; or with a reactive derivative thereof, to obtain compounds of the formula (I), wherein $R^1$, $R^2$, $R^3$ and the dotted lines are as defined above, R and $R^4$ are benzoyl group, a $C_{1-6}$alkanoyl group optionally substituted by a methoxy, cyano or carboxyl group, or by one or more halogen(s); and no double bond is present between the N(3) and C(4) atoms; or i) reacting a new compound of the formula (I), wherein R, $R^1$, $R^2$ and the dotted lines are as defined above, $R^3$ and $R^4$ are hydrogen and no double bond is present between the N(3) and C(4) atoms, with a $C_{1-5}$alkyl isocyanate or phenyl isocyanate, to obtain compounds of the formula (I), wherein $R^1$, $R^2$ and the dotted lines are as defined above, R is benzoyl group, a $C_{1-6}$alkanoyl group optionally substituted by a methoxy, cyano or carboxyl group, or by one or more halogen(s); $R^3$ is hydrogen; $R^4$ is a $C_{1-5}$alkylcarbamoyl or phenylcarbamoyl group and no double bond is present between the N(3) and C(4) atoms; or j) acylating a new compound of the formula (I), wherein $R^1$ $R^2$ and the dotted lines are as defined above, $R^3$ and $R^4$ are hydrogen and no double bond is present between the N(3) and C(4) atoms, with an N-phthaloylamino acid of the formula (VI), wherein $R^5$ is hydrogen or a $C_{1-4}$alkyl group and n is 1 in case of α-amino acids, whereas $R^5$ is hydrogen and n is an integer of 2 to 5 in case of β-ε-amino acids, and, if desired, removing the phthaloyl group, to obtain compounds of the formula (I), wherein $R^1$, $R^2$ and the dotted lines are as defined above, R is benzoyl group, a $C_{1-6}$alkanoyl group optionally substituted by a methoxy, cyano or carboxyl group or by one or more halogen(s), $R^3$ is hydrogen, $R^4$ is a $C_{1-6}$alkanoyl group substituted by an amino or phthalimido group and no double bond is present between the N(3) and C(4) atoms, and, if desired, transforming a base of the formula (I), obtained by any of the above processes a) to j), to an acid-addition salt.

According to a preferred embodiment of the process of the present invention the acylation of the compounds of the formula (I), (II), (III) and (V) can be carried out preferably with a suitable carboxylic acid, in the presence of dicyclohexyl-carbodiimide in a suitable solvent, preferably in dichloromethane, in a temperature range of 10° to 30° C. during 1 to 25 hours.

According to an other preferred embodiment of the present invention the compounds of the formula (I), (II), (III) and (V) can be acylated in a temperature range of zero to 150° C. by a suitable reactive acyl derivative, i.e. carboxylic acid anhydride, mixed anhydride or acyl chloride, in the absence or presence of a solvent usually applied in acylation reactions of such types like chloroform or dichloromethane, in the absence or presence of an acid-binding agent, such as triethylamine. If the additive acylation is performed with isocyanates, the reaction is preferably carried out in dimethylformamide, benzene or dichloromethane in a temperature range of 15° to 100° C. during 0.5 to 100 hours.

The selective reduction of the compound of the formula (IV) to the compound of the formula (V), wherein R is hydrogen atom, can be performed by an inorganic or inorganic-organic complex metal hydride, preferably sodium borohydride, in a solvent or solvent mixture which has no or only low reactivity to the complex metal hydride applied. In these reactions a $C_{1-4}$ alcohol or pyridine is the solvent of choice. (Similar selective reductions are described in the U.S. Pat. Nos. 4,423,044 and 4,835,152).

The nitro group of the new compounds of formula (V) is reduced to an amino group by hydrazine or hydrazine hydrate in the presence of a catalyst such as palladium, platinum or Raney nickel in a $C_{1-4}$ alcohol, dioxane, tetrahydrofuran, benzene, dimethylformamide, dimethylacetamide or in a mixture thereof.

According to a preferred embodiment of the process of the present invention the reduction can be carried out in methanol by hydrazine or hydrazine hydrate in the presence of Raney nickel catalyst in a temperature range of 10° to 65° C. (U.S. Pat. No. 4,614,740) but, if desired, the reduction and the removal of the phthaloyl protecting group described in process d) can be performed in the same vessel.

The N-phthaloylamino acids of the formula (IV) containing a chiral carbon atom, wherein $R^5$ is a $C_{1-4}$alkyl group and n is 1, can be prepared from DL-, L- and/or D-alpha-amino acids.

The compounds of the formula (I) of the invention, which contain a basic amino group, wherein $R^3$ and $R^4$ are hydrogen atom or R and/or $R^4$ are an aminoacyl group, can be transformed to their acid-addition salts by known methods.

The preparation of the compounds of the formula (II) used as starting materials in the process of the present invention is described in the U.S. Pat. No. 4,614,740, that of the compound of the formula (III), wherein $R^4$ is hydrogen atom, in the U.S. Pat. No. 4,835,152, while that of the compound of formula (IV) is published in the French patent specification No. 85,09793. The compounds of the formula (III), wherein $R^4$ is a $C_{1-6}$alkanoyl group, are new. The process for their preparation is described hereinafter, before Table 15, of they can be synthesized by methods indicated therein. The preparation of the new starting compounds of the formula (V) is described in the Examples. The ($\alpha$-$\epsilon$)-amino acid derivatives of the formula (VI) are prepared by methods known from the literature [J. Am. Chem. Soc. 35, 1133 (1913); 41, 845 (1919); Berichte der Deutschen Chemischen Gesellschaft 40, 498; 2649 (1907); 46, 1103; 3159 (1913); 47, 3166 (1914)] or by known methods using the reaction of phthalimide potassium with the required halocarboxylic acid.

Preferably, the selective reduction of the compound of the formula (IV) to the compound of the formula (V), wherein R is hydrogen atom, can be performed stereoselectively to produce either the (−) or (+) enantiomer. This enantioselective reduction uses a chiral hydride reagent, such as a chiral borane complex derivative. These chiral borane complexes are generally produced by the reaction of borane ($BH_3$) with a chiral 1,2-aminoaocohol. These preferred chiral boranes are prepared by the reaction of borane with 2-amino-3-methyl-1,1-diphenylbutan-1-ol, 2-amino-4-methyl-1,1-diphenylpentan-1-ol, or 2-amino-3-methyl-1,1-diphenylpentan-1-ol, that are readily prepared from valine, leucine, and isoleucine, respectively [J. Chem. Soc., Perkin Trans., 1, 2039 (1985)]. The most preferred chiral 1,2-aminoalcohol is (−) or (+)-2-amino-4-methyl-1,1-diphenylpentan-1-ol. The (+)-enantiomer of the formula (V) compound is prepared using the chiral boranes derived from D-valine, D-leucine, or D-isoleucine. Similarly, the (−)-enantiomer of the formula (V) compound is prepared using the chiral boranes derived from L-valine, L-leucine, or L-isoleucine. The reaction is typically carried out under dry nitrogen atmosphere in an organic solvent, such as dry dichloromethane or dry 1,2-dichloroethane, at a temperature of about 25° C. to 60° C. When the reaction is carried out in 1,2-dichloroethane at 60° C., using 1.5 equivalents of the chiral borane reagent, the reaction is complete after about 3 hours.

The compounds of the formula (I) of the present invention possess valuable central nervous system (CNS) activity such as inhibition of the activation of excitatory amino acid receptors as well as anticonvulsive, muscle-relaxant and neuroprotective effects, which can be shown by pharmacological tests.

For the comparison of the biological activity of the compounds of formula (I), 1-(4-aminophenyl)-4-methyl-7,8-methylenedioxy-5H-2,3-benzodiazepine (U.S. Pat. No. 4,614,740, in the following GYKI 52466), having related structure and qualitatively similar activity as the compounds of the present invention, was applied as reference compound, along with the competitive AMPA-antagonists CNQX (1,2,3,4-tetrahydro-7-nitro-2,3-dioxoquinoxalinecarbonitrile) and NBQX (1,2,3,4-tetrahydro-6-nitro-2,3-dioxo-benzo(f)quinoxaline-7-sulfonamide); the antiepileptic drugs phenytoin (5,5-diphenyl-2,4-imidazolidinedione) and the 1,4-benzodiazepine-type anticonvulsant diazepam (7-chloro-1,3-dihydro-1-methyl-5-phenyl-2H-1,4-benzodiazepin-2-one); the commonly used muscle-relaxant baclofen ($\beta$-(aminomethyl)-4-chlorobenzeneprioionic acid) and the neuroprotective agents MK-801 ((+)-10,11-dihydro-5-methyl-5H-dibenzo[a,d]cyclohepten-5,10-imine (Z)-2-butene-dioate), idebenone (2-(10-hydroxydecyl)-5,6-dimethoxy-3-methyl-2,5-cyclohexadiene-1,4-dione) and tirilazad (21-[4-(2,6-di-1-pyrrolidinyl-4-pyrimidinyl)-1-piperazinyl]-16-methyl-(16$\alpha$)-predna-1,4,9(11)-triene-3,20-dione).

The pharmacological effects of the compounds of the formula (I) are presented in Tables 1 to 13.

Inhibition of activation of AMPA receptors

Four experimental models were applied to demonstrate the blocking action of compounds of the formula (I) on the activation of AMPA receptors. In the first two models, their effects on predominantly AMPA receptor mediated synaptic responses were analysed. In the following two models neuronal depolarization and spreading depression evoked by glutamate agonists were studied.

Inhibition of synaptic field potentials in rat hippocampal slices

Synaptic potentials in the CA1 area of hippocampus evoked by stimulation of the Schaffer collaterals are mediated by AMPA/kainate receptors. AMPA antagonists dose-dependently inhibit these synaptic potentials. Inhibition of field potentials (population spikes) suggests an AMPA antagonist effect [Neurosci. Lett. 92, 64 (1988)].

The inhibition of population spikes in CA1 was studied in rat hippocampal slices after 30 min. perfusion application of the test compounds.

The results are shown in Table 1.

TABLE 1

| Inhibition of synaptic field potentials in rat hippocampal slices | |
|---|---|
| Compound Example No. | $IC_{50}$ ($\mu M$) |
| CNQX | 1.4 |
| GYKI 52466 | 31.7 |
| 15 (16) | 24.8 |
| 98 | 12.6 |
| 123 | 3.9 |
| 128 | 7.8 |

The $IC_{50}$ values of the most potent compounds are much lower than that of GYKI 52466, and are close to the competitive AMPA antagonist CNQX. Although CNQX is very effective in vitro, it is not suitable for therapeutic application, as its in vivo activity can only be detected after intra-cerebroventricular administration [Drugs of the Future 14, 667 (1989)].

Inhibition of synaptic field potentials in rat neocortex slices

Similarly as in hippocampal CA1 area, glutamate is the main excitatory transmitter in the neocortex, and dominantly AMPA receptors are involved in mediation of synaptic responses evoked by stimulation of the white matter and recorded from the area adjacent to the site of stimulation [J. Neurophysiol. 64, 1282 (1990)]. The inhibitory effect on such field potentials was studied in rat neocortex slices, maintained in Vitro, according to Fletcher et al. [Br. J. Pharmacol. 95, 585 (1988)].

The results are summarized in Table 2.

TABLE 2

Inhibition of synaptic field potentials in rat neocortex slices

| Compound Example No. | Concentration (μM) | Inhibition of induced field potentials in % of control | IC$_{50}$ (μM) |
| --- | --- | --- | --- |
| GYKI 52466 | 10 | 22 | |
| | 20 | 39 | |
| | 40 | 62 | 30.0 |
| | 80 | 73 | |
| 15 (16) | 10 | 30 | |
| | 20 | 47 | |
| | 40 | 69 | 21.5 |
| | 80 | 82 | |

Both GYKI 52466 and the compound of Example 15(16) inhibited AMPA receptor mediated synaptic field potentials, wherein the latter one was more potent.

Inhibition of AMPA receptor activation induced DC potentials in rat neocortex slices The AMPA antagonist effect was tested in rat neocortex slices by using a method similar to that of Harrison and Simmonds [Br. J. Pharmacol. 84, 381 (1985)]. In rat neocortex slices the DC-potential changes induced by perfusion of the AMPA receptor agonist quisqualate were dose-dependently inhibited by GYKI 52466 in the concentration range of 10–50 μM. At the corresponding concentrations, the compound of Example 15(16) proved to be twice as active as the reference compound in inhibiting the response to the 2-minute perfusion with 10 μM of quisqualate. However, both molecules failed to affect the responses induced by NMDA.

Inhibition of AMPA and kainate induced spreading depression in isolated chicken retina Anti-kainate and –AMPA effects were investigated in the in vitro retinal spreading depression model [Brain Res. 607, 189 (1993)]. AMPA/kainate antagonists prolong the latency of the development of spreading depression evoked by kainate (5 μM), or AMPA (5 μM). In some cases the effect on spreading depression evoked by 100 μM NMDA was also studied to clarify the selectivity.

The inhibitions obtained in the chicken retina model are presented in Table 3.

TABLE 3

Inhibition of AMPA and kainate induced spreading depression in isolated chicken retina

| Compound Example No. | AMPA IC$_{50}$ (μM) | Kainate IC$_{50}$ (μM) |
| --- | --- | --- |
| GYKI 52466 | 6.3 | 9.5 |
| 15 (16) | 3.7 | 5.1 |
| 123 | 1.7 | 0.5 |
| 128 | 1.0 | 2.7 |

Compounds of Example Nos. 128 and 123 were several times more potent inhibitors of retinal spreading depression than GYKI 52466. The NMDA antagonist effect of GYKI 52466 and that of the tested compounds of formula (I) was found to be about, or more than 10 times weaker than, their AMPA antagonist effect.

The results obtained in the four tests above, in which an inhibitory action on the consequences of either functional or direct activation of the AMPA receptors was demonstrated, suggest that the compounds of formula (I) have a selective AMPA antagonist effect. According to in vitro binding studies compounds of formula (I) displace neither [$^3$H]-AMPA nor [$^3$H]-kainate from their specific binding sites in CNS membrane preparations, similarly to GYKI 52466 [Neuroreport 5, 93 (1993)]. These results suggest that the novel compounds of formula (I) retained the non-competitive mode of action of GYKI 52466 [Neuron 10, 51 (1993); ibid. 10, 61 (1993)], which is mediated via an allosteric modulatory site at the AMPA receptor [Annu. Rep. Med. Chem. 29, 53 (1994)]. As it was discussed in the introductory part, drugs with a non-competitive action are advantageous over competitive blockers, as the blocking action of the latter ones can be overcome by extremely high agonist concentrations. This means that in cases of abnormally high extracellular concentrations of glutamate (which frequently occurs under pathological conditions), their convulsive or excitotoxic actions can still be exerted in the presence of competitive AMPA antagonists. The protective effect of the non-competitive antagonists, on the contrary, is basically independent from the concentration of glutamate.

Anticonvulsive activity

Although several drugs are applied for the therapy of epilepsy, these drugs have serious side effects, moreover there are certain forms of the disease which are not influenced by the presently available drug therapies. Thus, there is a need for new antiepileptic drugs with novel mechanism of action, and there is a great expectation to the introduction of agents that can limit glutamate-induced overexcitation of the central nervous system [TIPS 15, 456 (1994)].

Anticonvulsive effect in mice

The anticonvulsive effect of the compounds of the formula (I) was measured by using the electroshock test [J. Pharmacol. Exp. Ther. 106, 319 (1952)], furthermore by using various chemical agents such as pentetrazole [J. Pharmacol. Exp. Ther. 108, 168 (1953)], strychnine [J. Pharmacol. Exp. Ther. 129, 75 (1960)], bemegride, nicotine and 4-aminopyridine. The test compounds were orally administered in 3 doses, to 10 male CFLP mice per dose.

The results are presented in Table 4.

TABLE 4

Anticonvulsive effect in mice

| Compound Example No. | ED$_{50}$ p.o. (mg/kg) | | | | | |
| --- | --- | --- | --- | --- | --- | --- |
| | ES | Pentetrazole | Strychnine | Bemegride | Nicotine | 4-AP |
| Diazepam | 18 | 0.86 | 15 | 0.58 | 1.85 | |
| Phenytoin | 10 | >400 | 160 | >200 | 12 | |
| GYKI 52466 | 38 | 115 | 87 | 73 | 70 | 43 |
| 15 (16) | 12 | 46.8 | >200 | 16 | 45 | 9 |
| 18 | 17.5 | 29 | >100 | 20 | 16 | 16 |
| 39 | 53 | 170 | >200 | >200 | >200 | 29 |
| 42 | 24 | 33 | 28 | 24 | 155 | 34 |
| 45 | 27 | 44 | >100 | 51 | 23 | 34 |
| 46 | 20 | 57 | >100 | 56 | 80 | 17 |
| 48 | 10.5 | 30.5 | >100 | 33 | 25 | 20 |
| 49 | 25 | 53 | >100 | 43 | 45 | 28 |
| 52 | 17.5 | 36 | >100 | 29 | 13.5 | 24 |
| 60 | 24 | 62 | | | | |
| 62 | 12.5 | 56 | >100 | 36 | 31 | 29 |

TABLE 4-continued

Anticonvulsive effect in mice

| Compound Example No. | ED₅₀ p.o. (mg/kg) | | | | | |
|---|---|---|---|---|---|---|
| | ES | Pentet-razole | Strych-nine | Bemeg-ride | Nico-tine | 4-AP |
| 66 | 42 | 135 | 105 | >100 | 105 | 84 |
| 69 | 57 | >100 | | | | |
| 73 | 16 | 62 | >100 | 49 | 53 | 28 |
| 98 | 17.1 | 21.3 | 29 | 11 | 19 | 13.5 |
| 107 | 23.5 | 120 | 22.8 | 25.4 | 34.2 | 36.8 |
| 108 | 27 | >100 | | | | |
| 109 | 21 | >100 | | | | |
| 115 | 17.1 | 23.9 | | | | |
| 123 | 8.4 | 13.8 | | | | |
| 128 | 5.3 | 16.8 | | | | |

Abbreviations:
ES = electroshock
4-AP = 4-aminopyridine

The above data demonstrate that several compounds of the formula (I) possess wide-spectrum anticonvulsive effect even in comparison with the frequently used antiepileptic drug phenytoin. Although diazepam is the most effective in the majority of the tests, it is interesting to note that several compounds of the invention are superior to it in the maximal electroshock test, and it is well known that the application of 1,4-benzodiazepine-type anticonvulsants is limited because of their addictive properties [Pharmacol. Rev. 39, 251 (1987)].

The anticonvulsive activity of several test compounds (e.g. of Examples 15(16), 42, 45, 46, 73, 98, 107, 108, 109, 115, 123 and 128) is superior to that of GYKI 52466.

Muscle-relaxant activity

Centrally acting muscle-relaxant drugs are used in clinical situations when muscular trauma, spinal cord or brain lesions, or chronic neurological diseases result in symptoms like increased resting tone of skeletal muscles, hyperreflexia, or tremor. Muscle spasms are frequently painful and hinder the normal movements.

The muscle-relaxant activity of the compounds of formula (I) was measured in four tests.

In Randall's inclined screen test [J. Pharmacol. Exp. Ther. 129, 163 (1960)] the compounds were applied in 3 i.p. doses to 10 CFLP mice per dose.

The results are shown is Table 5.

TABLE 5

Inclined screen test in mice

| Compound Example No. | ED₅₀ i.p. (mg/kg) |
|---|---|
| Baclofen | 26 |
| GYKI 52466 | 47 |
| 15 (16) | 23.5 |
| 18 | 31 |
| 42 | 42 |
| 45 | 35 |
| 48 | 20.5 |
| 49 | 36 |
| 52 | 21 |
| 62 | 25.5 |
| 66 | 52 |
| 73 | 27 |
| 98 | 18 |

TABLE 5-continued

Inclined screen test in mice

| Compound Example No. | ED₅₀ i.p. (mg/kg) |
|---|---|
| 115 | 16.1 |
| 123 | 8.8 |
| 128 | 13.4 |

The rotarod test was used to measure muscular tone and motor co-ordination [J. Am. Pharm. Assoc. 46, 208 (1957)].

The results are presented in Table 6.

TABLE 6

Rotarod test in mice

| Compound Example No. | ED₅₀ i.p. (mg/kg) |
|---|---|
| Baclofen | 12.5 |
| GYKI 52466 | 24.0 |
| 15 (16) | 3.7 |
| 18 | 7.5 |
| 42 | 8.1 |
| 45 | 10 |
| 48 | 7.2 |
| 49 | 9.4 |
| 52 | 4.8 |
| 62 | 7.8 |
| 66 | 18.5 |
| 73 | 6.3 |
| 98 | 8.6 |
| 115 | 7.3 |
| 123 | 1.9 |
| 128 | 2.3 |

Most clinically active muscle-relaxants inhibit segmental spinal reflexes including flexor reflex [Pharm. Res. Comm. 20, S1, 141 (1988)].

The effect on spinal function was studied with the most active compounds of the formula (I) and two reference compounds. Table 7 shows the effect on polysynaptic flexor reflexes in chloralose anaesthetized cats [Pharm. Res. Comm. 20, S1, 141 (1988)].

TABLE 7

Effect on spinal flexor reflexes, in cats

| Compound Example No. | ED₅₀ (mg/kg, i.v.) |
|---|---|
| NBQX | 0.91 |
| GYKI 52466 | 0.90 |
| 15 (16) | 0.36 |
| 98 | 0.14 |
| 123 | 0.05 |
| 128 | 0.13 |

Tables 5, 6 and 7 demonstrate that several compounds of formula (I) possess strong muscle-relaxant activity (e.g. compounds of Examples 15(16), 18, 42, 45, 48, 49, 62, 73, 98, 115, 123 and 128).

The effect of compound of Example 15(16) on the spinal root potentials in cats was tested in spinalized and immobilized animals [Neuropharmacology 21, 161 (1989)].

The result is presented in Table 8.

TABLE 8

Effects on spinal root reflex potentials in cats

| Compound Example No. | $ED_{50}$ (mg/kg, i.v.) | | | |
|---|---|---|---|---|
| | MSR | PSR | DRR | DRP |
| GYKI 52466 | 2.20 | 2.30 | >4* | >4* |
| 15 (16) | 0.69 | 0.77 | >1.6* | >1.6* |

Abbreviations:
*<20% inhibition at the highest dose applied;
MSR = monosynaptic ventral root reflex;
PSR = polysynaptic ventral root reflex;
DRR = dorsal root reflex;
DRP = dorsal root potential The other reference compound, diazepam, did not affect monosynaptic reflexes (up to 3.2 mg/kg), partially (max. 50%) inhibited polysynaptic reflexes (minimal effective dose below 0.1 mg/kg), and markedly potentiated both dorsal root responses (minimal effective doses around 0.1 mg/kg).

These results indicate that GYKI 52466 and compounds of formula (I) have a strong action on ventral root reflex potentials, compound of Example 15(16) is more effective than GYKI 52466.

The effects of the compounds of formula (I) in the above assays of muscle-relaxant activity indicate that they have a potential therapeutic value in treating diseases and conditions associated with increased muscular tone.

Neuroprotective activity

Acute and chronic neurodegenerative diseases of diverse origin have similarities in the mechanism leading to cell death. The role of glutamate-mediated excitotoxicity and the increase of intracellular calcium concentration seem to be common features in diseases and conditions like stroke, brain injury, global brain ischaemia after cardiac arrest, Parkinson's disease, etc. This fact suggests that inhibition of glutamate-mediated neurotoxicity can be a successful strategy in the treatment of neurodegenerative disorders.

Neuroprotective effect of compounds of the formula (I) following transient (4 min.) occlusion of both carotid arteries was tested in conscious mice. This transient carotis occlusion (global ischaemia) model, mimics the problems occurring during and after cardiac arrest, in humans. Retention of memory was tested in a passive avoidance task performed 24 h after reperfusion [J. Pharm Meth. 23, 311 (1990)].

The results are shown in Table 9.

TABLE 9

Protection against memory impairment caused by transient bilateral carotis occlusion, in conscious mice

| Compound Example No. | Doses which resulted in significant protective effect |
|---|---|
| Tirilazad | 50 mg/kg i.p. |
| Idebenone | 50 mg/kg i.p. |
| 15 (16) | 20 mg/kg p.o. |
| 98 | 20 mg/kg p.o. |
| 123 | 10 mg/kg p.o. |

The data demonstrate that the compounds listed in Table 9 significantly prevented animals from functional deficit caused by transient global ischaemia.

Potassium cyanide (10 mg/kg i.v.) causes lethality which occurs usually within 22 sec. [Meth. Find. Exptl. Clin. Pharmacol. 10, 349 (1988)], neuroprotective compounds prolong the survival time. The compounds of the formula (I) were tested by this method to demonstrate their neuroprotective ability.

The results are presented in Table 10.

TABLE 10

Protection against KCN intoxication, in mice

| Compound Example No. | Doses which resulted in significant protective effect |
|---|---|
| Tirilazad | 100 mg/kg i.p. |
| Idebenone | 100 mg/kg i.p. |
| GYKI 52466 | 40 mg/kg p.o. |
| 15 (16) | 50 mg/kg p.o. |
| 98 | 10 mg/kg p.o. |
| 123 | 10 mg/kg p.o. |

The compounds of Examples 15(16), 98 and 123 included in Table 10 exerted a statistically significant protective effect.

AMPA injected (2.5 nmol in 0.25 µl) into the striatum of seven-day-old rats causes marked tissue lesion [Brain Res. 526, 165 (1990)]. When the animals were treated with the compounds of the formula (I) (four times, hourly), the tissue lesion was reduced.

The results are shown in Table 11.

TABLE 11

Protection against AMPA induced neuronal damage in the striatum of young rats

| Compound Example No. | Doses which resulted in significant protective effect |
|---|---|
| GYKI 52466 | 4 × 10 mg/kg i.p. |
| 15 (16) | 4 × 4 mg/kg i.p. |
| 98 | 4 × 4 mg/kg i.p. |
| 123 | 4 × 2 mg/kg i.p. |
| 128 | 4 × 2 mg/kg i.p. |

The data of Table 11 demonstrate that the efficacy of several compounds of the formula (I) is superior to that of the reference compound GYKI 52466.

One of the methods for modelling chronic neurodegenerative disorders associated with dopaminergic dysfunction is methamphetamine-induced neurotoxicity.

High doses of methamphetamine (2×20 mg/kg i.p.) decrease the striatal level of dopamine, which can be prevented by glutamate antagonists, e.g. the NMDA-antagonist MK-801 [Science 243, 398 (1989)].

Experiments were performed with compound of Example 128 (3×5 mg/kg, i.p.) to demonstrate its ability to prevent methamphetamine-induced striatal dopamine loss and the increase in striatal dopamine turnover rate.

The results are presented in Table 12.

TABLE 12

Protection against methamphetamine-induced dopaminergic neurotoxicity, in mice

| Treatment | DA, μg/g tissue mean ± SE | % | (DOPAC + HVA)/DA mean ± SE | % |
|---|---|---|---|---|
| Saline | 15.09 ± 0.74 | 100 | 0.25 ± 0.04 | 100 |
| METH + saline | 1.58 ± 0.25 | 10 | 0.97 ± 0.15 | 388 |
| METH + MK-801 | 10.01 ± 1.10 | 66 | 0.33 ± 0.06 | 132 |
| METH + 128 | 7.17 ± 1.89 | 48 | 0.36 ± 0.10 | 144 |

Abbreviations:
DA = dopamine;
DOPAC = dihydrophenylacetic acid;
HVA = homovanillic acid;
METH = methamphetamine The data of Table 12 show that the compound of Example 128 exerted a protective effect against dopaminergic neurotoxicity, which is comparable to the effect of the NMDA antagonist MK-801 (3×2.5 mg/kg, i.p.). This result indicates that the compounds of the formula (I) may be useful in the treatment of chronic neurological disorders such as Parkinson's disease.

In conclusion, the positive results in the four models discussed above are indicative of a therapeutic potential of compounds of the formula (I) in treating acute and chronic neurodegenerative disorders.

Mutagenicity

The mutagenic effect of GYKI 52466 and of compounds of the formula (I) of the invention was tested in the Ames test in vitro on four of the Salmonella typhimurium strains (TA 97/a; TA 98; TA 100; TA 102), with or without previous metabolic activation (incubation with rat liver microsomes), according to Maron and Ames [Mutation Res. 113, 173 (1983)]. Compounds were dissolved in DMSO and applied up to the maximal achievable concentration. Compounds which significantly elevated the spontaneously occurring mutation rate of the bacteria at more than one concentrations in at least one bacterium strain, either with or without metabolic activation, were regarded as Ames positive. As a result of these studies GYKI 52466 was found to be Ames positive, while the novel derivatives of the formula (I) were found to be Ames negative.

Acute toxicity data obtained in mice are summarized in Table 13.

TABLE 13

| Compound | Acute toxicity in mice | |
|---|---|---|
| | $LD_{50}$ (mg/kg) | |
| Example No. | p.o. | i.p. |
| 15 (16) | 129.5 | 127.2 |
| 39 | >600 | 271 |
| 42 | 185.4 | 119.7 |
| 45 | 206.1 | 98.4 |
| 46 | 162.0 | 173.3 |
| 48 | 149.0 | 103.2 |
| 52 | 187.5 | 117.1 |
| 62 | 159.7 | 136.5 |
| 66 | 280.6 | 204.9 |
| 73 | 167.7 | 143.1 |
| 98 | 96.6 | 93.1 |

TABLE 13-continued

| Compound | Acute toxicity in mice | |
|---|---|---|
| | $LD_{50}$ (mg/kg) | |
| Example No. | p.o. | i.p. |
| 115 | 200–250 | 90.7 |
| 123 | 75–100 | ≈50 |
| 128 | ≈100 | 73.5 |

At toxic dose levels the compounds induced a dose-dependent muscle tone reduction, ataxia, adynamia, and loss of the righting reflex. The cause of mortality was respiratory insufficiency developing within 1 to 2 hours after i.p. administration and within 10 to 20 hours after oral application.

Based on the above pharmacological results, the compounds of the formula (I) according to the invention possess significant excitatory amino acid-antagonist, anticonvulsive, muscle-relaxant and neuroprotective effects. Thus, they are therapeutically useful for the treatment of epilepsy as well as various diseases connected with spasms of the skeletal musculature or acute and chronic neurodegenerative disorders such as cerebral ischaemia. (stroke).

The invention also relates to pharmaceutical compositions containing compounds of general formula (I) or pharmaceutically acceptable acid-addition salts thereof as active ingredients as well as to the preparation of these compositions.

For therapeutical use, the active compounds according to the invention are suitably formulated to pharmaceutical compositions by admixing them with commonly used nontoxic, inert, solid or liquid pharmaceutical carriers and/or auxiliary materials useful for enteral or parenteral administration. As carriers, e.g. water, gelatine, lactose, starch, pectin, magnesium stearate, stearic acid, talc or vegetable oils can be used. As auxiliary materials, e.g. preservatives and wetting as well as emulsifying, dispersing and aromatizing agents and buffers can be employed.

By using the above-mentioned carriers and auxiliary materials, the active agents of the invention may be transformed to the usual pharmaceutical compositions, e.g. to solid compositions (such as tablets, capsules, pills or suppositories) or liquid compositions (such as aqueous or oily solutions, suspensions, emulsions or syrups) as well as to injectable solutions, suspensions or emulsions.

For therapeutical purposes, the daily dose of the compounds of the invention amounts commonly 0.01 to 2, preferably to 0.2–1.5 mg/kg of body weight which is administered daily, optionally divided to several doses.

Based on the above facts, the present invention also provides:
- a method of blocking the activation of one or more excitatory amino acid receptors in mammals. This method comprises administering to a mammal in need of such treatment a pharmaceutically effective amount of a compound of the formula (I);
- a method of treating epilepsy in mammals. This method comprises administering to a mammal in need of such treatment an antiepileptic amount of a compound of the formula (I);
- a method of treating spasms of the skeletal musculature in mammals. This method comprises administering to a mammal in need of such treatment a muscle-relaxing amount of a compound of the formula (I);
- a method of treating acute and chronic neurodegenerative disorders in mammals. This method comprises administering to a mammal in need of such treatment a pharmaceutically effective amount of a compound of the formula (I).

The compounds prepared by the process of the invention were identified by elementary analysis, their purity and structure were controlled and confirmed by thin-layer chromatography, HPLC, IR, 1H-NMR, 13C-NMR and mass spectrometry.

The invention is illustrated in detail by the following non-limiting Examples.

EXAMPLE 1

1-(4-Diacetylaminophenyl)-3-acetyl-4-methylene-7,8-methylenedioxy-4,5-dihydro-3H-2,3-benzodiazepine 2.93 g (0.01 mol) of 1-(4-aminophenyl)-4-methyl-7,8-methylenedioxy-5H-2,3-benzodiazepine were refluxed with 20 ml of acetic anhydride for 6 hours. The solution was evaporated at reduced pressure, the residue was taken up in 2×20 ml of anhydrous ethanol, the solution was repeatedly evaporated and the resulting residue of 4.55 g was submitted to column chromatography (adsorbent: Kieselgel 60, eluant: ethyl acetate—benzene 4:1). The raw produce was triturated with 20 ml of hot isopropanol to yield 1.44 g (34.4%) of the aimed product, m.p. 240°–245° C. (slight decomp.).

$C_{23}H_{21}N_3O_5=419,445$

EXAMPLE 2

1-(4-Formylaminophenyl)-4-methyl-7,8-methylenedioxy-5H-2,3-benzodiazepine 3.0 g (10.2 mmol) of 1-(4-aminophenyl)-4-methyl-7,8-methylenedioxy-5H-2,3-benzodiazepine were dissolved in 160 ml of dichloromethane and first 2.75 g (13.3 mmol) of dicyclohexylcarbodiimide, then 0.51 ml (13.3 mmol) of 100% formic acid were added and the reaction mixture was stirred for 2 hours at room temperature. The precipitated N,N'-dicyclohexylurea was filtered, the filtrate was extracted with 2×30 ml of 10% aqueous sodium carbonate solution, then with 2×30 ml of distilled water, the organic layer was dried and evaporated at reduced pressure. The residue was dissolved in ethyl acetate, filtered and evaporated under reduced pressure. The resulting raw product was recrystallized from 20 ml of 50% ethanol to yield 2.93 g (89.3%) of the aimed product, m.p. 152°–154° C. (slight decomp.).

$C_{18}H_{15}N_3O_3=321.342$

EXAMPLES 3 to 7

The compounds of Examples 3 to 7 were prepared by the process described in Example 2.

EXAMPLE 3

1-(4-Cyanoacetylaminophenyl)-4-methyl-7,8-methylene-dioxy-5H-2,3 benzodiazepine $C_{20}H_{16}N_4O_3=360.380$, m.p.: 241°–243° C. (decomp.)

EXAMPLE 4

1-(4-Methoxyacetylaminophenyl)-4-methyl-7,8-methylene-dioxy-5H-2,3-benzodiazepine $C_{20}H_{19}N_3O_4=365.396$, m.p.: 203°–205° C.

EXAMPLE 5

1-(4-Valerylaminophenyl)-4-methyl-7,8-methylenedioxy-5H-2,3-benzodiazepine $C_{22}H_{23}N_3O_3=377.450$, m.p.: 217°–219° C. (decomp.)

EXAMPLE 6

1-(4-Phenylacetylaminophenyl)-4-methyl-7,8-methylenedioxy-5H-2,3-benzodiazepine $C_{25}H21N_3O_3=411.467$, m.p.: 245°–247° C. (decomp.).

EXAMPLE 7

1-(4-Cyclopropanecarbonylaminophenyl)-4-methyl-7,8-methylenedioxy-5H-2,3-benzodiazepine $C_{21}H_{19}N_3O_3=361.407$, m.p.: 260°–262° C. (decomp.).

EXAMPLE 8

1-(4-Acetylaminophenyl)-4-methyl-7,8-methylenedioxy-5H-2,3-benzodiazepine 10 g (34 mmol) of 1-(4-aminophenyl)-4-methyl-7,8-methylenedioxy-5H-2,3-benzodiazepine were stirred for 3 hours with 100 ml of acetic anhydride. The crystals formed were filtered, washed with 5×10 ml of anhydrous ethanol and dried, yielding 9.2 g of raw product, m.p. 252°–254° C. (decomp.). This product was treated with 45 ml of hot 99.5% ethanol. After cooling the crystals were filtered, washed with 3×10 ml of ethanol and dried to give 8.68 g (76.1%) of the aimed product, m.p.: 256°–258° C.(decomp.).

$C_{19}H_{17}N_3O_3=335.369$

EXAMPLE 9

1-(4-Propionylaminophenyl)-4-methyl-7,8-methylenedioxy-5H-2,3-benzodiazepine $C_{20}H_{19}N_3O_3=349.396$, m.p.: 228°–230° C. (decomp.).

It was prepared by the process described in Example 8.

EXAMPLE 10

1-(4-Pivaloylaminophenyl)-4-methyl-7,8-methylenedioxy-5H-2,3-benzodiazepine 1.56 ml (11.2 mmol) of triethylamine and 1.38 ml (11.2 mmol) of pivaloyl chloride were added to a solution of 3 g (10.2 mmol) of 1-(4-aminophenyl)-4-methyl-7,8-methylenedioxy-5H-2,3-benzodiazepine in 160 ml of dichloromethane and the reaction mixture was stirred at 25° C. for one hour. The precipitate formed Was filtered, washed with 3×5 ml of dichloromethane, then with 3×20 ml of water and dried to yield 1.59 g of pure product, m.p. 225°–227° C. (decomp.). The other portion of the product was isolated from the organic phase. The filtrate was extracted with 3×20 ml of water, then with 3×15 ml of 4% aqueous sodium hydroxide solution, finally with 2×30 ml of water. The organic layer was subsequently dried and evaporated under reduced pressure. The crystalline residue was combined with the former product of 1.59 g and suspended in 20 ml of hot ethanol. The product was filtered after cooling, washed with 3×3 ml of ethanol and dried to yield 3.38 g (87.8%) of the pure product, m.p.: 225°–227° C. (decomp.).

$C_{22}H_{23}N_3O_3=377.450$

EXAMPLE 11

1-(4-Benzoylaminophenyl)-4-methyl-7,8-methylenedioxy-5H-2,3-benzodiazepine 1.0 ml (15 mmol) of benzoyl chloride and 2.1 ml (15 mmol) of triethylamine were added to a solution of 4 g (13.6 mmol) of 1-(4-aminophenyl)-4-methyl-7,8-methylenedioxy-5H-2,3-benzodiazepine in dichloromethane and the reaction mixture was stirred at 25° C. for 24 hours. The solution was extracted with 3×30 ml of water, 3×20 ml of a 4% aqueous sodium hydroxide solution and finally with 2×30 ml of distilled water. The organic layer was dried, evaporated under reduced pressure, then the crystalline residue was treated with 20 ml of hot ethanol to obtain 3.97 g of raw product, m.p. 242°–243° C. This raw product was repeatedly treated with 20 ml of hot ethanol, next day it was filtered at 0–5° C., washed with 3×3 ml of ethanol and dried at 100° C. to yield 3.85 g (71.3%) of the pure aimed product, m.p. 246°–247° C. (decomp.).

$C_{24}H_{19}N_3O_3=397.40$

EXAMPLE 12

1-(4-Palmitoylaminophenyl)-4-methyl-7,8-methylenedioxy-5H-2,3-benzodiazepine

By following the process described in Example 11, with recrystallization of the raw product from 50% ethanol, the pure aimed product was obtained, m.p. 138°–140° C.

$C_{33}H_{45}N_3O_3=531.747$

EXAMPLE 13

1-(4-Phenylcarbamoylaminophenyl)-4-methyl-7,8-methylenedioxy-5H-2,3-benzodiazepine 0.22 ml (2.04 mmol) of phenyl isocyanate was added to a solution of 0.50 g (1.7 mmol) of 1-(4-aminophenyl)-4-methyl-7,8-methylenedioxy-5H-2,3-benzodiazepine in 4 ml of dimethylformamide and the reaction mixture was stirred at 25° C. for one hour. Then it was diluted with 20 ml of diethyl ether and filtered at 5° C. The crystals were washed with 2×5 ml of diethyl ether and dried at 60°–100° C. The resulting 0.70 g of raw product, m.p. 239°–240° C. (sintering at 180° C.) was refluxed in 15 ml of ethanol, filtered after cooling, washed with 3×1 ml of ethanol and dried at 100° C. to yield 0.55 g (78.6%) of the aimed product, m.p. 240°–241° C. (decomp.).

$C_{24}H_{20}N_4O_3=412.456$

EXAMPLE 14

1-[4-(4-Carboxybutyrylamino)phenyl]-4-methyl-7,8-methylenedioxy-5H-2,3-benzodiazepine A solution of 0.50 g (1.7 mmol) of 1-(4-aminophenyl)-4-methyl-7,8-methylenedioxy-5H-2,3-benzodiazepine in 30 ml of anhydrous dichloromethane was stirred with 0.18 g (1.87 mmol) of glutaric acid anhydride at 20°–25° C. for 6 hours. Next day the crystals formed were filtered at 0°–5° C., washed with 3×2 ml of dichloromethane and dried at 60°–80° C. to give 0.60 g (87.0%) of the pure aimed product, m.p. 225°–227° C. (decomp.).

$C_{22}H_{21}N_3O_5=407.434$

EXAMPLE 15

1-(4-Aminophenyl)-3-acetyl-4-methyl-7,8-methylenedioxy-5H-2,3-benzodiazepine

To a solution of 3.58 g (12.1 mmol) of 1-(4-aminophenyl)-4-methyl-7,8-methylenedioxy-3,4-dihydro-5H-2,3-benzodiazepine in 100 ml of chloroform first 1.68 ml (12.1 mmol) of triethylamine, then under constant ice-cooling and stirring 1.15 ml (12.1 mmol) of acetic anhydride were added.

Stirring was continued for additional 2 hours, then the solution was extracted with 3×100 ml of water, the organic layer was dried and evaporated under reduced pressure. The crystalline residue was recrystallized from 40 ml of isopropanol to obtain 3.50 g (85.7%) of the aimed product, m.p. 220°–222° C. After repeated recrystallization the m.p. increased to 223°–225° C.

$C_{19}H_{19}N_3O_3=337.385$

Hydrochloride: $(C_{19}H_{20}N_3O_3)Cl=373.850$, m.p.: 248°–252° C. (decomp.).

EXAMPLE 16

1-(4-Aminophenyl)-3-acetyl-4-methyl-7,8-methylenedioxy-3,4-dihydro-5H-2,3-benzodiazepine To a suspension of 1.91 g (5.37 mmol) of 1-(4-nitrophenyl)-3-acetyl-4-methyl-7,8-methylenedioxy-3,4-dihydro-5H-2,3-benzodiazepine (product of Example 27) in 40 ml of methanol about 0.2 g of Raney nickel catalyst and 1.4 ml (28 mmol) of 100% hydrazine hydrate were added, then the reaction mixture was stirred at 20°–25° C. for one hour. The starting nitro derivative was dissolved within 10–20 minutes. After filtering the filtrate was evaporated under reduced pressure, the white crystalline residue was washed with 30 ml of distilled water onto a filter, it was washed with 3×10 ml of distilled water and dried at 100° C. to give 1.50 g of a raw product, m.p. 218°–220° C. This raw product was purified by treating with 12 ml of hot isopropanol. After cooling it was filtered at 5° C., washed with 3×1 ml of isopropanol and dried at 100° C. to yield 1.40 g (77.35%) of a white crystalline powder, m.p. 221°–223° C. On the basis of analyses and spectra it was identical to the product of Example 15 obtained by a different process.

EXAMPLE 17 to 25

The process described in Example 16 was followed for preparing other 1-(4-aminophenyl)-3-R-4-methyl-7,8-methylenedioxy-3,4-dihydro-5H-2,3-benzodiazepines of the general formula (I). The data of the products prepared are presented in Table 14.

TABLE 14

| Products of the general formula (I) wherein $R_2 = CH_3$ and $R_1 = R_3 = R_4 = H$ | | |
|---|---|---|
| Example No. | R | M.p. °C. |
| 17 | Trifluoroacetyl | 215–217 |
| 18 | Propionyl | 211–213 |
| 19 | Valeryl | 178–180 |
| 20 | Pivaloyl | 233–235 (d) |
| 21 | Benzoyl | 220–222 |
| 22 | Phenylacetyl | 220–221 |
| 23 | Cyclopropylcarbonyl | 138–140 |
| 24 | Cyanoacetyl | 123–126 |
| 25 | Methoxyacetyl | 125–127 |

(d) = decomposition

The new nitro compounds of the general formula (V), wherein R=H or an optionally substituted $C_{1-6}$alkanoyl group, used in the preparation of products of Examples 16 to 25, can be prepared by processes described in Examples 26 to 36.

EXAMPLE 26

1-(4-Nitrophenyl)-4-methyl-7,8-methylenedioxy-3,4-dihydro-5H-2,3-benzodiazepine

To a suspension of 5.0 g (15.5 mmol) of the known 1-(4-nitrophenyl-4-methyl-7,8-methylenedioxy-5H-2,3- benzodiazepine (French patent specification No. 85,09793) in 380 ml of ethanol first 22.5 ml (0.278 mol) of concentrated hydrochloric acid were added at constant stirring whereupon a solution was formed within a few minutes, then 11.5 g (0.3 mole) of sodium borohydride were charged into the solution portionwise during 30 minutes. Stirring was continued for 15 minutes, then the orange-coloured precipitate formed was filtered and extracted on the filter with 4×30 ml of chloroform. The combined chloroform filtrate was evaporated under reduced pressure, the crystalline residue was brought to a filter with 200 ml of distilled water, then washed with 3×20 ml of distilled Water and dried at 80°–100° C. to yield 4.90 g (97.2%) of the aimed product, m.p.: 162°–164° C.

$C_{17}H_{15}N_3O_4 = 325.331$

EXAMPLE 27

1-(4-Nitrophenyl)-3-acetyl-4-methyl-7,8-methylenedioxy-3,4-dihydro-5H-2,3-benzodiazepine A 2.0 g (6.15 mmol) portion of the product of Example 26 was stirred with 10 ml of acetic anhydride at 25° C. for 3 hours then 50 ml of distilled water were added and the stirring was continued for one hour. The yellow precipitate formed was filtered, washed with 3×10 ml of distilled water and dried at 80°–100° C. to obtain 2.6 g of raw product. After recrystallization from 10 ml of ethanol 1.94 g (85.8%) of the aimed product were obtained, m.p.: 140°–142° C.

$C_{19}H_{17}N_3O_5 = 367.369$

EXAMPLE 28

1-(4-Nitrophenyl)-3-trifluoroacetyl-4-methyl-7,8-methylenedioxy-3,4-dihydro-5H-2,3-benzodiazepine To a solution of a 1.5 g (4.61 mmol) portion of the product of Example 26 is in 30 ml of anhydrous dichloromethane 0.75 ml (5.3 mmol) of trifluoroacetic acid anhydride and 0.75 ml (5.3 mmol) of triethylamine were added and the reaction mixture was stirred at 25° C. for 3 hours. Subsequently, the mixture was extracted with 3×20 ml of water and the organic layer was dried and evaporated under reduced pressure. The crystalline residue was treated with 15 ml of hot ethanol, cooled, filtered, washed with 3×1 ml of ethanol and dried at 80°–100° C. to yield 1.84 g (94.85%) of the aimed compound as a bright yellow crystalline product, m.p.: 165°–167° C. (decomp.).

$C_{19}H_{14}F_3N_3O_5 = 421.339$

EXAMPLE 29

1-(4-Nitrophenyl)-3-propionyl-4-methyl-7,8-methylenedioxy-3,4-dihydro-5H-2,3-benzodiazepine A 1.54 g (4.7 mmol) portion of the product of Example 26 was stirred with 8 ml of propionic acid anhydride at 25° C. for 3 hours, then 30 ml of diethyl ether were added and the solution was kept at 0°–5° C. overnight. The precipitate formed was filtered, washed with 3×8 ml of diethyl ether and dried to yield 1.32 g (73.7%) of the aimed compound as a light yellow product, m.p.: 189°–190° C.

$C_{20}H_{19}N_3O_5 = 381.396$

EXAMPLE 30

1-(4-Nitrophenyl)-3-valeryl-4-methyl-7,8-methylenedioxy-3,4-dihydro-5H-2,3-benzodiazepine To a solution of a 2.5g (7.68 mmol) portion of the product of Example 26 in 40 ml of anhydrous dichloromethane 4.75 g (23 mmol) of dicyclohexylcarbodiimide and 2.88 g (23 mmol) of n-valeric acid were added and the reaction mixture was maintained at 25° C. under intermittent stirring for 24 hours. Then the N,N'-dicyclohexylurea formed as by-product was filtered, the filtrate was evaporated under reduced pressure, the residue was mixed with 2×40 ml of distilled water, decanted and the wet product was left to solidify under 50 ml of 50% ethanol. The solid compound was filtered, washed with 2×10 ml of 50% ethanol and dried at 80° C. The raw product obtained was recrystallized from 24 ml of ethanol and the crystals were dried at 100° C. to yield 2.20 g (70%) of the aimed product as a yellow powder, m.p.: 145°–147° C.

$C_{22}H_{23}N_3O_5 = 409.450$

EXAMPLE 31

1-(4-Nitrophenyl)-3-pivaloyl-4-methyl-7,8-methylenedioxy-3,4-dihydro-5H-2,3-benzodiazepine By following the process described in Example 28 but applying pivaloyl chloride instead of trifluoroacetic acid anhydride, 1.68 g (89.4%) of the aimed product were obtained, m.p.: 164°–166° C.

$C_{22}H_{23}N_3O_5 = 409.450$

EXAMPLE 32

1-(4-Nitrophenyl)-3-benzoyl-4-methyl-7,8-methylenedioxy-3,4-dihydro-5H-2,3-benzodiazepine By following the process described in Example 31 but using benzoyl chloride as acyl chloride, 1.72 g (86.9%) of an ochre yellow product were obtained, m.p.: 222°–224° C. (decomp.).

$C_{24}H_{19}N_3O_5 = 429.440$

EXAMPLE 33

1-(4-Nitrophenyl)-3-phenylacetyl-4-methyl-7,8-methylenedioxy-3,4-dihydro-5H-2,3-benzodiazepine By following the process described in Example 30 but using 50% of the calculated molar amount of dicyclohexylcarbodiimide and phenylacetic acid, a bright yellow product was obtained, m.p.: 193°–195° C.

$C_{25}H_{21}N_3O_5 = 443.467$

EXAMPLES 34 to 36

The products of Examples 34 to 36 were obtained by following the process described in Example 33 and using the respective acid components.

EXAMPLE 34

1-(4-Nitrophenyl)-3-cyclopropanecarbonyl-4-methyl-7,8-methylenedioxy-3,4-dihydro-5H-2,3-benzodiazepine M.p.: 225°–228° C. (decomp.).

$C_{21}H_{19}N_3O_5 = 393.407$

EXAMPLE 35

1-(4-Nitrophenyl)-3-cyanoacetyl-4-methyl-7,8-methylenedioxy-3,4-dihydro-5H-2,3-benzodiazepine M.p.: 185°–188° C.

$C_{20}H_{16}N_4O_{05} = 392.380$

EXAMPLE 36

1-(4-Nitrophenyl)-3-methoxyacetyl-4-methyl-7,8-methylenedioxy-3,4-dihydro-5H-2,3-benzodiazepine M.p.: 187°–189° C.

$C_{20}H_{19}N_3O_6=397.396$

EXAMPLE 37

1-(4-Nitrophenyl)-3-(4-carboxybutyryl)-4-methyl-7,8-methylenedioxy-3,4-dihydro-5H-2,3-benzodiazepine By using the product of Example 26 as starting material and performing the acylation according to Example 14 with glutaric acid anhydride, finally recrystallizing the raw product from ethanol the pure aimed product was obtained, m.p.: 148°–150° C.

$C_{22}H_{21}N_3O_7=439.434$

EXAMPLE 38

1-(4-Aminophenyl)-3-phenylcarbamoyl-4-methyl-7,8-methylendioxy-3,4-dihydro-5H-2,3-benzodiazepine To a solution of 0.70 g (2.3 mmol) of 1-(4-aminophenyl)-4-methyl-7,8-methylenedioxy-3,4-dihydro-5H-2,3-bemzodiazepine in 10 ml of anhydrous benzene 0.24 ml (2.3 mmol) of phenyl isocyanate was added and the reaction mixture was refluxed for one hour. Thereafter the solution was evaporated under reduced pressure and the amorphous residue was mixed with 20 ml of hot 50% ethanol. The suspension was cooled to 0° C. and filtered to yield 0.76 g of a raw product, m.p. 190°–200° C. After recrystallization from 99.5% ethanol and trituration with ethyl acetate the aimed compound melts at 207°–209° C.

$C_{24}H_{22}N_4O_3=414.472$

The preparation of the starting material of this example was described in the Hungarian patent specification No. 198,494. However, the compound may also be prepared by a new method according to the process of Example 16, by using the compound of Example 26 as starting material to give excellent yields (84%). The raw product may be recrystallized from 50% ethanol, m.p.: 118°–120° C.

EXAMPLE 39

1-(4-Diacetylaminophenyl)-3-acetyl-4-methyl-7,8-methylenedioxy-3,4-dihydro-5H-2,3-benzodiazepine 2.0 g (6.7 mmol) of 1-(4-aminophenyl)-4-methyl-7,8-methylenedioxy-3,4-dihydro-5H-2,3-benzodiazepine were refluxed with 40 ml of acetic anhydride for 3 hours, then it was evaporated to dryness under reduced pressure. The crystalline residue was transferred with 25 ml of water to a filter and washed with 5×3 ml of water. After drying 2.79 g of the raw triacetyl derivative were obtained. After washing with 20 ml of isopropanol and drying at 100° C. 2.39 g (84.6 of the pure aimed product were obtained, m.p. 224°–227° C.

$C_{23}H_{23}N_3O_5=421,461$

EXAMPLE 40

$N^1$-[4-(3-Acetyl-4-methyl-7,8-methylenedioxy-3,4-dihydro-5H-2,3-benzodiazepin-1-yl)-phenyl]-$N^3$-methylurea 0.70 g (2 mmol) of the product of Example 15 was dissolved in benzene dehydrated over calcium hydride, 0.3 ml (5 mmol) of methyl isocyanate was added and the reaction mixture was stirred at 50° C. for 4 hours. The crystals formed after cooling were filtered, washed with 3×3 ml of benzene, then triturated with 20 ml of hot benzene. The hot mixture was filtered, the precipitate was washed with 3×3 ml of benzene and dried to give 0.65 g (79.6%) of the aimed product, m.p.: 168°–170° C. (decomp.).

$C_{21}H_{22}N_4O_4=394.439$

EXAMPLE 41

$N^1$-[4-(3-Acetyl-4-methyl-7,8-methylenedioxy-3,4-dihydro-5H-2,3-benzodiazepin-1-yl)-phenyl]-$N^3$phenylurea By following the process described in Example 40 but using phenyl isocyanate instead of methyl isocyanate, refluxing the reaction mixture for 10 hours, evaporating it under reduced pressure, then suspending the residue first in 50 ml of diethyl ether and then in 15 ml of ethyl acetate, 0.69 g (75.7%) of the aimed product was obtained, m.p.: 184°–186° C. (decomp.).

$C_{26}H_{24}N_4O_4=456.510$

EXAMPLE 42

1-(4-Acetylaminophenyl)-3-acetyl-4-methyl-7,8-methylenedioxy-3,4-dihydro-5H-2,3-benzodiazepine 1.3 g (4.4 mmol) of 1-(4-aminophenyl)-3-acetyl-4-methyl-7,8-methylenedioxy-3,4-dihydro-5H-2,3-benzodiazepine were stirred at 20°–25° C. with 5 ml of acetic anhydride for one hour, then the yellow solution was poured into 100 g of ice-water and stirred until the decomposition of the excess anhydride became complete. The precipitate formed was filtered, washed with 3×10 ml of distilled water and dried to give 1.6 g of raw product. After recrystallization from 20 ml of benzene 1.50 g (89.85%) of the aimed product were obtained, m.p.: 158°–160° C. (decomp.).

$C_{21}H_{21}N_3O_4=379.423$

EXAMPLE 43

1-(4-Formylaminophenyl)-3-formyl-4-methyl-7,8-methylenedioxy-3,4-dihydro-5H-2,3-benzodiazepine To 6.0 ml (0.104 mol) of acetic anhydride 3.0 ml (0.08 mol) of 100% formic acid were added dropwise at 0° C. during 5 minutes while constant stirring. The stirring was continued at 50° C. for 15 minutes. Thereafter 1 g (3.3 mmol) of 1-(4-aminophenyl)-4-methyl-7,8-methylenedioxy-3,4-dihydro-5H-2,3-benzodiazepine was added to the thus-prepared mixed anhydride. The reaction mixture was stirred at 25° C. for 1.5 hours, then poured into ice-water, the precipitate formed was filtered, washed with 4×5 ml of distilled water and dried at 80° C. to give 0.80 g of raw product. After crystallization from 3 ml of ethyl acetate 0.65 g (56.2%) of the aimed product was obtained, m.p.: 193°–195° C.

$C_{19}H_{17}N_3O_4=351.369$

EXAMPLE 44

1-(4-Trifluoroacetylaminophenyl)-3-trifluoroacetyl-4-methyl-7,8-methylenedioxy-3,4-dihydro-5H-2,3-benzodiazepine 1.48 g (5 mmol) of 1-(4-aminophenyl)-4-methyl-7,8-methylenedioxy-3,4-dihydro-5H-2,3-benzodiazepine were dissolved in 30 ml of anhydrous chloroform, then 2.1 ml (15 mmol) of triethylamine and at 20°–25° C. 2.12 ml (15 mmol) of trifluoroacetic anhydride were added and the reaction mixture was stirred for 2.5 hours, then extracted first with 2×30 ml of water and thereafter with 20 ml of 5% hydrochloric acid. The organic layer was dried over anhydrous sodium sulfate, evaporated under reduced pressure and the amorphous residue was recrystallized from 10 ml of 70% ethanol to give 1.41 g (57.9%) of the aimed diacyl derivative, m.p. 177°–178° C.

$C_{21}H_{15}F_6N_3O_4 = 487.363$

EXAMPLE 45

1-(4-Propionylaminophenyl)-3-propionyl-4-methyl-7,8-methylenedioxy-3,4-dihydro-5H-2,3-benzodiazepine The process described in Example 44 was followed, except that 11.2 mmol of both triethylamine and propionic acid anhydride were used and the crystalline residue was recrystallized first from 15 ml of 50% ethanol, then from 11.5 ml of 99% ethanol to give 2.48 g (60.9%) of the aimed product, m.p.: 152°–154° C.

$C_{23}H_{25}N_3O_4 = 407.477$

EXAMPLES 46 to 65

Other diacyl derivatives of the general formula (I), wherein R=optionally substituted $C_{1-6}$ alkanoyl group, $R^1=R^3=H$, $R^2=CH_3$ and $R^4=$ optionally substituted $C_{1-6}$ alkanoyl group, where R and $R^4$ are the same or different, are presented in Table 15. These compounds were prepared partly from compounds of the general formula (III), wherein $R=R^1=R^3=H$ and $R^4=$ optionally substituted $C_{1-6}$ alkanoyl group; and partly from new compounds of the general formula (I), wherein R=optionally substituted $C_{1-6}$ alkanoyl group, $R^1=R^3=R^4=H$ and $R^2=CH_3$, according to processes defined in the preceding examples.

The preparation of starting substances of general formula (III), wherein $R=R^1=R^3=H$ and $R^4=$ optionally substituted $C_{1-6}$ alkanoyl group is illustrated in detail below on the derivative bearing acetyl group as $R^4$:

1-(4-Acetylaminophenyl)-4-methyl-7,8-methylenedioxy-3,4-dihydro-5H-2,3-benzodiazepine Method A):

To a solution containing 6.0 g (20 mmol) 1-(4-aminophenyl)-4-methyl-7,8-methylenedioxy-3,4-dihydro-5H-2,3-benzodiazepine in 30 ml of ethyl acetate 1.38 ml (21 mmol) of methanesulfonic acid were added. The crystalline precipitate was filtered and washed with 5×5 ml of ethyl acetate. The dry weight of the product was 7.37 g, m.p.: it sintered above 190° C. and weakly decomposed at 210°–212° C. The thusobtained methanesulfonate salt of the starting substance was acetylated as follows:

7.37 g of the powdered salt were suspended in 110 ml of acetic anhydride, the suspension was stirred at room temperature for 2 hours, then the crystalline precipitate was filtered, washed with 5×10 ml of ethyl acetate and dried to give 6.54 g of methanesulfonate salt of the target compound, m.p. 240°–241° C. (with decomposition).

The base was liberated from the methanesulfonate salt of the target compound e.g. in the following way: 6.54 g of salt were dissolved in 90 ml of water, the solution was clarified by charcoal, then 3.6 g of sodium hydrogen carbonate were portionwise added to the clear solution. The precipitate was filtered, washed with 5×10 ml of water and dried to obtain 5.54 g of crude product. After recrystallization from 130 ml of isopropanol, 3.11 g (yield 46%) of product were obtained, m.p.: 221°–223° C. (weak decomposition), the melting point of which increased to 223°–225° C. after digesting with 15 ml of hot benzene.

$C_{19}H_{19}N_3O_3 = 337.385$

The hydrochloride salt decomposed at 262°–264° C.

Method B)

After dissolving 15.0 g (44.7 mmol) of 1-(4-acetylaminophenyl)-4-methyl-7,8-methylenedioxy-5H-2,3-benzodiazepine in 150 ml of pyridine under mild heating, 10.2 g (0.269 mol) of sodium borohydride were added and the mixture was stirred on an oil bath at a temperature of 100° C. for 5 hours. Then the reaction mixture was cooled to about 25° C., 150 ml of water were dropwise added under continuous stirring during 20 minutes, thereafter a mixture containing 180 ml of concentrated hydrochloric acid and 265 ml of water was added while cooling with ice-water. A yellowish suspension was formed. The precipitate was filtered, washed with 5×20 ml of water and dried to yield 15.2 g of salt, m.p. above 250° C. In order to liberate the base, this salt was suspended in 150 ml of 50% ethanol and then 5.7 g of sodium hydrogen carbonate were portionwise added while stirring. The thusformed suspension was filtered after 30 minutes, washed successively with 3×10 ml of 50% ethanol, 5×20 ml of water, finally with 20 ml of 50% ethanol and dried to obtain 10.95 g of a crude product, m.p.: 218°–220° C. (weak decomposition). After digesting this crude product with 50 ml of hot isopropanol and then with 100 ml of hot 99.5% ethanol, 8.63 g (57.2%) of the aimed compound were obtained, m.p.: 220°–222° C. (weak decomposition).

Physical characteristics of other 1-(4-acylaminophenyl)-4-methyl-7,8-methylenedioxy-3,4-dihydro-5H-2,3-benzodiazepine are as follows:

| $R^4$-Analogue | M.p. °C. |
| --- | --- |
| Propionyl | 237–239 |
| Benzoyl | 247–248 (decomp.) |
| Phenylacetyl | 213–215 (decomp.) |
| Pivaloyl | 132–135 (decomp.) |

TABLE 15

Compounds of the general formula (I), wherein $R^1 = R^3 = H$, $R^2 = CH_3$,
R and $R^4$ are optionally substituted $C_{1-6}$ alkanoyl groups

| Example No. | R | $R^4$ | Starting material Example No. | Process of Example No. | M.p. °C. |
|---|---|---|---|---|---|
| 46 | COCH$_3$ | CHO | 15 (16) | 2, 30 | 142–144 |
| 47 | COCF$_3$ | COCH$_3$ | (III), $R^4$ = COCH$_3$ | 28, 44 | 212–214 |
| 48 | COCH$_3$ | COC$_2$H$_5$ | 15 (16) | 28, 44 | 155–157 |
| 49 | COC$_2$H$_5$ | COCH$_3$ | (III), $R^4$ = COCH$_3$ | 28, 44 | 168–170 |
| 50 | COCH$_3$ | CO—C(CH$_3$)$_3$ | 15 (16) | 31 | 201–203 |
| 51 | CO—C(CH$_3$)$_3$ | COCH$_3$ | (III), $R^4$ = COCH$_3$ | 31 | 138–140 |
| 52 | COCH$_3$ | CO—CH$_2$—OCH$_3$ | 15 (16) | 2, 30 | 118–120 |
| 53 | CO—CH$_2$OCH$_3$ | COCH$_3$ | (III), $R^4$ = COCH$_3$ | 2, 30 | 136–138 (d) |
| 54 | COCH$_3$ | CO—CH$_2$—CN | 15 (16) | 2, 30 | 149–151 (d) |
| 55 | CO—CH$_2$—CN | COCH$_3$ | (III), $R^4$ = COCH$_3$ | 2, 30 | 128–130 (d) |
| 56 | CO—C$_6$H$_5$ | COCH$_3$ | (III), $R^4$ = COCH$_3$ | 31 | 154–156 |
| 57 | COCH$_3$ | CO—C$_6$H$_5$ | 15 (16) | 31 | 214–216 |
| 58 | CO—(CH$_2$)$_3$—COOH | COCH$_3$ | (III), $R^4$ = COCH$_3$ | 14 | 172–174 |
| 59 | COCH$_3$ | CO—(CH$_2$)$_3$—COOH | 15 (16) | 14 | 210–212 (d) |
| 60 | CHO | COC$_2$H$_5$ | (III), $R^4$ = COC$_2$H$_5$ | 2 | 185–187 |
| 61 | CHO | CO—C(CH$_3$)$_3$ | (III), $R^4$ = CO—C(CH$_3$)$_3$ | 2 | 220–221 (d) |
| 62 | COCH$_3$ | COCF$_3$ | 15 (16) | 28 | 150–152 (d) |
| 63 | CHO | CO—C$_6$H$_5$ | (III), $R^4$ = CO—C$_6$H$_5$ | 2 | 202–203 (d) |
| 64 | COCH$_3$ | CO—CH$_2$—C$_6$H$_5$ | (III), $R^4$ = CO—CH$_2$—C$_6$H$_5$ | 2 | 135–137 |
| 65 | COC$_2$H$_5$ | CHO | 18 | 2 | 140–141 (d) |

(d) = decomposition

EXAMPLE 66

1-(4-Glycylaminophenyl)-4-methyl-7,8-methylenedioxy-5H-2,3-benzodiazepine

To a suspension of 2.89 g (5.97 mmol) of 1-(4-phthaloylglycylaminophenyl)-4-methyl-7,8-methylenedioxy-5H-2,3-benzodiazepine (Example 79) in 50 ml of methanol 0.6 ml (11.9 mmol) of 100% hydrazine hydrate was added and the mixture was refluxed for 2 hours. The reaction mixture was cooled, evaporated under reduced pressure, the partially crystalline residue was mixed with 40 ml of dichloromethane, filtered and the by-product was washed with 2×10 ml of dichloromethane. The solution was extracted with 3×15 ml of 5% hydrochloric acid, the aqueous layer was made alkaline with 24 ml of aqueous 10% sodium hydroxide, the precipitate formed was filtered, washed with 3×10 ml of distilled water and dried at 100° C. to obtain 1.67 g of raw product. After recrystallization from 73 ml of ethanol 1.50 g (71.8%) of the aimed product were obtained, m.p.: 223°–225° C.

$C_{19}H_{18}N_4O_3$=350.385

EXAMPLES 67 to 78

Other compounds of the general formula (I), wherein $R^2$=CH$_3$, $R^3$=H, and some of their acid addition salts, prepared by the process of Example 66, are presented in Table 16. The salts were prepared by known methods.

TABLE 16

| Example No. | R | $R^1$ | $R^4$ | Example No. of starting material | M.p. °C. (salt) |
|---|---|---|---|---|---|
| 67 | — | — | CO—(CH$_2$)$_3$—NH$_2$ | 80 | 198–200 (d) |
| 68 | — | — | DL—CO—CH(CH$_3$)—NH$_2$ | 81 | 155–157 (d) |
| 69 | — | — | DL—CO—CH(CH$_3$)—NH$_2$ | 68 | 217–219 (d) (H—Fu) |
| 70 | CO—CH$_2$—NH$_2$ | H | H | 82 | 150–155 |
| 71 | CO—CH$_2$—NH$_2$ | H | H | 70 | 190–193 (d) (H—Fu) |
| 72 | DL—CO—CH(CH$_3$)—NH$_2$ | H | H | 84 | 193–195 (H—Fu 210–213 (d)) |
| 73 | COCH$_3$ | H | CO—CH$_2$—NH$_2$ | 88 | 210–211 (d) (HCl) [base 230–232 (d)] |
| 74 | CO—CH$_2$—CH$_2$ | H | COCH$_3$ | 89 | 210–212 (d) |
| 75 | CO—(CH$_2$)$_3$—NH$_2$ | H | COCH$_3$ | 90 | 154–156 (d) (Fu) |
| 76 | (H—Fu), COCH$_3$ | H | DL—CO—CH(CH$_3$)—NH$_2$ | 91 | 222–223 (d) (H—Fu) |
| 77 | DL—CO—CH(CH$_3$)—NH$_2$ | H | COCH$_3$ | 92 | 218–220 (d) |
| 78 | CO—CH$_2$—NH$_2$ | H | CO—CH$_2$—NH$_2$ | 93 | 202–204 (d) |

Notes:
H—Fu = hydrogen fumarate (H-fumarate),
Fu = fumarate
The products of Examples 70 to 72 were prepared from the corresponding starting substances in two steps, by following first Example 66 and then Example 16.

EXAMPLE 79

1-[4-(N-Phthaloylglycylamino) phenyl]-4-methyl-7,8-methylenedioxy-5H-2,3-benzodiazepine To a solution of 2.0 g (6.88 mmol) of 1-(4-aminophenyl)-4-methyl-7,8-methylenedioxy-5H-2,3-benzodiazepine in dichloromethane 1.84 g (8.94 mmol) of dicyclohexylcarbodiimide and 1.84 g (8.94 mmol) of powdered phthalimidoacetic acid were added and the reaction mixture was stirred at 25° C. for 8 hours, then left to stand at 0°–5° C. overnight. The precipitate formed was filtered, washed with 3×3 ml of dichloromethane and dried at 60°–80° C. to result in 5 g of a product consisting of a mixture of the target product and N,N'-dicyclohexylurea, a by-product. This mixture was purified by refluxing with 210 ml of ethanol for 30 minutes, filtering the hot mixture and washing with 2×10 ml of hot ethanol, thereafter drying at 100° C. to obtain 2.42 g (73.3% of the aimed product, m.p.: 266°–268° C. (decomp.).

$C_{27}H_{20}N_4O_5=480.489$

EXAMPLE 80

1-[4-(N-Phthaloyl-γ-aminobutyrylamino)phenyl]-4-methyl-7,8-methylenedioxy-5H-2,3-benzodiazepine By following the process described in Example 79 but using -phthalimidobutyric acid, 3.8 g of a mixture were obtained, which was combined with the dichloromethane mother liquor extracted previously with 2×40 ml of a 10% aqueous sodium carbonate solution. After evaporating under reduced pressure the residue was submitted to column chromatography (adsorbent: Kieselgel 60 (0.063–2 mm), eluant: ethyl acetate-methanol 4:1). The evaporation residue was triturated with 10 ml of hot ethanol, cooled, filtered, washed with 3×1 ml of ethanol and dried to give 3.12 g (90%) of the aimed product, m.p.: 233°–235° C. (decomp.).

$C_{29}H_{24}N_4O_5=508.543$

EXAMPLE 81

1-[4-(N-Phthaloyl-DL-alanylamino)phenyl]-4-methyl-7,8-methylenedioxy-5H-2,3-benzodiazepine The process described in Example 79 was followed, except that N-phthaloyl-DL-alanine (DL-2-phthalimidopropionic acid) was used. After filtering the slight precipitate formed the filtrate was evaporated, the residue was mixed with 15 ml of dichloromethane, carefully filtered and the clear solution obtained was repeatedly evaporated. The purification of the residue was achieved by refluxing it with 60 ml of ethyl acetate. Crystal formation was already started in the hot solution. The crystals were filtered at 0°–5° C., the nearly white crystal powder was washed with 3×3 ml of ethyl acetate and dried at 100° C. to give 2.75 g (80.95%) of the aimed product, m.p.: 243°–245° C. (decomp.).

$C_{28}H_{22}N_4O_5=494.516$

EXAMPLE 82

1-(4-Nitrophenyl)-3-glycyl-4-methyl-7,8-methylenedioxy-3,4-dihydro-5H-2,3-benzodiazepine The process described in Example 66 was followed by using the compound prepared according to Example 85 as starting material, but the-dichloromethane solution was extracted only with 3×20 ml of distilled water and the organic layer was evaporated under reduced pressure. The crystalline residue was purified by suspending it in 7 ml of ethanol to give the pure aimed product in a yield of 86.1%, m.p.: 201°–203° C. (decomp.).

$C_{19}H_{18}N_4O_5=382.385$

EXAMPLE 83

1-(4-Nitrophenyl)-3-(γ-aminobutyryl)-4-methyl-7,8-methylenedioxy-3,4-dihydro-5H-2,3-benzodiazepine By following the process described in Example 82 and using the compound prepared according to Example 86 as starting material, a product containing crystal solvent was obtained in a yield of 89.4%, m.p. 110°–112° C. (recrystallized from 50% ethanol).

$C_{21}H_{22}N_4O_5=410.439$

EXAMPLE 84

1-(4-Nitrophenyl)-3-(DL-alanyl)-4-methyl-7,8-methylenedioxy-3,4-dihydro-5H-2,3-benzodiazepine By following the process described in Example 82 and using the compound prepared according to Example 87 the aimed compound was obtained, m.p. 220°–221° C. (decomp.).

$C_{20}H_{20}N_4O_5=396.412$

EXAMPLES 85 to 87

The new intermediates employed in Examples 82 to 84 as starting materials were prepared from the compound prepared according to Example 26 by the process of Example 81.

EXAMPLE 85

1-(4-Nitrophenyl)-3-(N-phthaloylglycyl)-4-methyl-7,8-methylenedioxy-3,4-dihydro-5H-2,3-benzodiazepine Yield: 93.3%, m.p.: 173°–174° C. (decomp.).

$C_{27}H_{20}N_4O_7=512.489$

EXAMPLE 86

1-(4-Nitrophenyl)-3-(N-phthaloyl-γ-aminobutyryl)-4-methyl-7,8-methylenedioxy-3,4-dihydro-5H-2,3-benzodiazepine M.p.: 218°–220° C.

$C_{29}H_{24}N_4O_7=540.543$

EXAMPLE 87

1-(4-Nitrophenyl)-3-(N-phthaloyl-DL-alanyl)-4-methyl-7,8-methylenedioxy-3,4-dihydro-5H-2,3-benzodiazepine M.p.: 210°–212° C.

$C_{28}H_{22}N_4O_7=526.516$

EXAMPLE 88 to 94

The intermediates of the general formula (I), wherein R and/or $R^4$ represent(s) a $C_{1-6}$alkanoyl group substituted by a phthalimido group, are required for the preparation of compounds obtained by using the processes of Examples 73 to 78 and summarized in Table 17. They were prepared from the compound of Example 15 (16) or from a compound of the general formula (III), wherein $R_4$ is hydrogen (see U.S. Pat. No. 4,835,152) or from 1-(4-acetylaminophenyl)-4-methyl-7,8-methylenedioxy-3,4-dihydro-5H-2,3-benzodiazepine described hereinabove (before Table 15) by following the process of Example 81.

As a matter of course, in Example 93 a twofold amount of phthaloylglycine and dicyclohexylcarbodiimide have to be used. Thus, Table 17 lists new compounds of the general formula (I), wherein R and $R^1$ are optionally substituted $C_{1-6}$alkanoyl groups, $R^1=R^3=H$ and $R^2=CH_3$.

The crystalline residue was triturated with 30 ml of hot ethanol at 80° to 100° C. to obtain 3.35 g (95%) of the lemon-yellow aimed product, m.p.: 238°–240° C. (decomp.).

$C_{19}H_{18}N_4O_5=382.385$

TABLE 17

| Example No. | R | $R^4$ | M.p. °C. |
|---|---|---|---|
| 88 | COCH₃ | CO—CH₂—N(CO)₂C₆H₄ | 314–316 (d) |
| 89 | CO—CH₂—N(CO)₂C₆H₄ | COCH₃ | 204–206 (d) |
| 90 | CO—(CH₂)₃—N(CO)₂C₆H₄ | COCH₃ | 150–152 |
| 91 | COCH₃ | DL—CO—CH(CH₃)—N(CO)₂C₆H₄ | 264–266 (d) |
| 92 | DL—CO—CH(CH₃)—N(CO)₂C₆H₄ | COCH₃ | 245–248 |
| 93 | CO—CH₂—N(CO)₂C₆H₄ | CO—CH₂—N(CO)₂C₆H₄ | 230–232 (d) |
| 94 | COCH₃ | CO—(CH₂)₃—N(CO)₂C₆H₄ | 173–175 |

(CO)₂C₆H₄ = phthaloyl;
N(CO)₂C₆H₄ = phtalimido;
(d) = decomposition

EXAMPLE 95

1-(4-Aminophenyl)-3-(γ-aminobutyryl)-4-methyl-7,8-methylenedioxy-3,4-dihydro-5H-2,3-benzodiazepine hydrogen fumarate It was prepared from the compound of Example 83 by following Example 16, m.p.: 150°–152° C. (decomp.)

$[C_{29}H_{25}N_4O_3].C_4H_3O_4=496.531$

EXAMPLE 96

1-(4-Aminophenyl)-3-(4-carboxybutyryl)-4-methyl-7,8-methylenedioxy-3,4-dihydro-5H-2,3-benzodiazepine hydrochloride It was obtained from the compound of Example 37, according to Example 16, m.p.: 224°–226° C. (decomp.).

$[C_{22}H_{24}N_3O_5]Cl=445.915$

EXAMPLE 97

1-(4-Trifluoroacetylaminophenyl)-4-methyl-7,8-methylenedioxy-5H-2,3-benzodiazepine It was prepared by following Example 2, m.p.: 258°–260° C. (decomp.).

$C_{19}H_{14}F_3N_3O_3=389.339$

EXAMPLE 98

1-(4-Aminophenyl)-3-methylcarbamoyl-4-methyl-7,8-methylenedioxy-3,4-dihydro-5H-2,3-benzodiazepine It was prepared from 1-(4-nitrophenyl)-3-methylcarbamoyl-4-methyl-7,8-methylenedioxy-3,4-dihydro-5H-2,3-benzodiazepine according to Example 16, m.p. 199°–201° C.

$C_{19}H_{20}N_4O_3=352.401$

Hydrochloride m.p. 219°–221° C. (decomp.).

$[C_{19}H_{21}N_4O_3]Cl=388.86$

The starting nitro compound was prepared as follows:

1.1 ml (18.4 mmol) of methyl isocyanate were added to 3.0 g (9.22 mmol) of 1-(4-nitrophenyl)-4-methyl-7,8-methylenedioxy-3,4-dihydro-5H-2,3-benzodiazepine (see Example 26) dissolved in 60 ml of dichloromethane and stirred for 24 hours, then evaporated under reduced pressure.

EXAMPLE 99

1-(4-Aminophenyl)-3-(1-pyrrolidinoacetyl)-4-methyl-7,8-methylenedioxy-3,4-dihydro-5H-2,3-benzodiazepine It was obtained from 1-(4-nitrophenyl)-3-(1-pyrrolidinoacetyl)-4-methyl-7,8-methylenedioxy-3,4-dihydro-5H-2,3-benzodiazepine by following Example 16, m.p.: 212°–214° C.

$C_{23}H_{26}N_4O_3=406.493$

The starting substance was obtained from 1-(4-nitrophenyl)-3-chloroacetyl-4-methyl-7,8-methylenedioxy-3,4-dihydro-5H-2,3-benzodiazepine (see Example 116) according to Example 102, m.p.: 189°–190° C. (decomp.).

$C_{23}H_{24}N_4O_5=436.477$

EXAMPLE 100

1-(4-Aminophenyl)-3-(N,N-dimethylglycyl)-4-methyl-7,8-methylenedioxy-3,4-dihydro-5H-2,3-benzodiazepine hydrogen fumarate It was prepared from 1-(4-nitrophenyl)-3-(N,N-dimethylglycyl)-4-methyl-7,8-methylenedioxy-3,4-dihydro-5H-2,3-benzodizapine according to Example 16, m.p.: 202°–204° C. (decomp.).

$[C_{21}H_{25}N_4O_3]C_4H_3O_4=496.531$

The starting substance was obtained from 1-(4-nitrophenyl)-3-chloroacetyl-4-methyl-7,8-methylenedioxy-3,4-dihydro-5H-2,3-benzodiazepine according to the process described in Example 103, m.p.: 158°–160° C.

$C_{21}H_{22}N_4O_5=410.439$

EXAMPLE 101

1-(4-Chloroacetylaminophenyl)-4-methyl-7,8-methylenedioxy-5H-2,3-benzodiazepine

It was prepared according to Example 2, except that chloroacetic acid was used, m.p.: 209°–214° C. (carbonization).

$C_{19}H_{16}ClN_3O_3=369.818$

EXAMPLE 102

1-[4-(1-Pyrrolidinoacetylamino)phenyl]-4-methyl-7,8-methylenedioxy-5H-2,3-benzodiazepine 0.71 ml (8.53 mmol) of pyrrolidine was added to a suspension of 1.5 g (406 mmol) of 1-(4-chloroacetylaminophenyl)-4-methyl-7,8-methylenedioxy-5H-2,3-benzodiazepine in 60 ml of ethanol and the reaction mixture was refluxed for 4 hours, then evaporated under reduced pressure. The residue was treated with water to give a rough product (1.49 g), m.p.: 186°–188° C. After recrystallization from 12 ml of ethanol 1.22 g (74.4%) of the aimed product were obtained, m.p.: 210°–212° C.

$C_3H_{24}N_4O_3=404\ 477$

EXAMPLE 103

1-[4-(N,N-dimethylglycylamino) phenyl]-4-methyl-7,8-methylenedioxy-5H-2,3-benzodiazepine After adding 0.66 g (8.12 mmol) of dimethylamine hydrochloride and 1.86 ml (13.4 mmol) of triethylamine to a suspension of 1.5 g (4.06 mmol) of 1-(4-chloroacetylaminophenyl)-4-methyl-7,8-methylenedioxy-5H-2,3-benzodiazepine in 60 ml of ethanol, the reaction mixture was refluxed for 8 hours, then evaporated. The residue was dissolved in 30 ml of dichloromethane, washed with 20 ml of 4% NaOH solution, then 2×20 ml of distilled water, dried and evaporated under reduced pressure. After treating with water, the crystalline residue was filtered to give 1.27 g of raw product, m.p. 211°–213° C. After recrystallization from 10 ml of ethanol 1.1 g (71.4%) of aimed product were obtained, m.p.: 213°–215° C.

$C_{21}H_{22}N_4O_6=378.439$

EXAMPLE 104

1-(4-Methylcarbamoylaminophenyl)-4-methyl-7,8-methylenedioxy-5H-2,3-benzodiazepine 0.8 ml (13.4 mmol) of methyl isocyanate was added to a solution containing 1.0 g (3.41 mmol) of 1-(4-aminophenyl)-4-methyl-7,8-methylenedioxy-5H-2,3-benzodiazepine in 8 ml of dimethylformamide (DMF), then the reaction mixture was stirred at 25° C. for 24 hours. After diluting with 80 ml of water, filtering at 5° C. and drying at 60 to 100° C., 1.06 g of raw product, m.p.: 204°–207° C. (sintering from 160° C.) were obtained which, when recrystallized from 5 ml of ethanol, gave 0.85 g (71.4%) of-the aimed product, m.p.: 223°–224° C. (decomp.).

$C_{19}H_{18}N_4O_3=350.385$

EXAMPLE 105

1-(4-Acetylaminophenyl)-3-methylcarbamoyl-4-methyl-7,8-methylenedioxy-3,4-dihydro-5H-2,3-benzodiazepine It was prepared from 1-(4-aminophenyl)-3-methylcarbamoyl-4-methyl-7,8-methylenedioxy-3,4-dihydro-5H-2,3-benzodiazepine by using the process of Example 42. The raw product was recrystallized from ethyl acetate to give 71.4% of the aimed product, m.p.: 150°–152° C.

$C_{21}H_{22}N_4O_4=394.439$

EXAMPLE 106

1-(4-Chloroacetylaminophenyl)-3-acetyl-4-methyl-7,8-methylenedioxy-3,4-dihydro-5H-2,3-benzodiazepine It was prepared from 1-(4-aminophenyl)-3-acetyl-4-methyl-7,8-methylenedioxy-3,4-dihydro-5H-2,3-benzodiazepine by using the process of Example 2, m.p.: 139°–140° C.

$C_{21}H_{20}ClN_3O_4=413.972$

EXAMPLE 107

1-[4-(N,N-dimethylglycylamino)phenyl]-3-acetyl-4-methyl-7,8-methylenedioxy-3,4-dihydro-5H-2,3-benzodiazepine It was prepared from the product of the preceding Example by using the process described in Example 103, m.p.: 206°–208° C.

$C_{23}H_{26}N_4O_4=422.493$

EXAMPLE 108

1-[4-(N,N-diethylglycylamino)phenyl]-3-acetyl-4-methyl-7,8-methylenedioxy-3,4-dihydro-5H-2,3-benzodiazepine It was prepared from 1-(4-chloroacetylaminophenyl)-3-acetyl-4-methyl-7,8-methylenedioxy-3,4-dihydro-5H-2,3-benzodiazepine and diethylamine by using the process described in Example 102, m.p.: 175°–176° C.

$C_{25}H_{30}N_4O_4=450.547$

EXAMPLE 109

1-[4-(1-Pyrrolidinoacetylamino)phenyl]-3-acetyl-4-methyl-7,8-methylenedioxy-3,4-dihydro-5H-2,3-benzodiazepine hydrogen fumarate It was prepared from 1-(4-chloroacetylaminophenyl)-3-acetyl-4-methyl-7,8-methylenedioxy-3,4-dihydro-5H-2,3-benzodiazepine by using the process of Example 2 and isolated is the form of hydrogen fumarate, m.p.: 181°–183° C. (decomp.).

$[C_{25}H_{29}N_4O_4]C_4H_3O_4=564.607$

EXAMPLE 110

1-(4-Acetylaminophenyl)-3-chloroacetyl-4-methyl-7,8-methylenedioxy-3,4-dihydro-5H-2,3-benzodiazepine It was prepared from the compound of general formula (III), wherein $R^4=COCH_3$, by using the process of Example 2 and chloroacetic acid instead of formic acid, m.p. 138°–140° C.

$C_{21}H_{20}ClN_3O_4=413.972$

EXAMPLE 111

1-[4-(N,N-diethylglycylamino)phenyl]-4-methyl-7,8-methylenedioxy-5H-2,3-benzodiazepine It was prepared from 1-(4-chloroacetylaminophenyl)-4-methyl-7,8-methylenedioxy-5H-2,3-benzodiazepine by using the process of Example 102, except that diethylamine was used instead of pyrrolidine, m.p.: 157°–158° C.

$C_{23}H_{26}N_4O_3=406.493$

EXAMPLE 112

1-(4-Acetylaminophenyl)-3-cyclopropanecarbonyl-4-methyl-7,8-methylenedioxy-3,4-dihydro-5H-2,3-benzodiazepine It was prepared from 1-(4-aminophenyl)-3-cyclopropanecarbonyl-4-methyl-7,8-methylenedioxy-3,4-dihydro-5H-2, 3-benzodiazepine by using the process of Example 42, m.p.: 242°–243° C.

$C_{23}H_{23}N_3O_4=405.461$

EXAMPLE 113

$N^1$-[4-(3-Methylcarbamoyl-4-methyl-7,8-methylenedioxy-3,4-dihydro-5H-2,3-benzodiazepin-1-yl)phenyl]-$N^3$-methylurea After adding 0.5 ml (8.5 mmol) of methyl isocyanate to 0.6 g (1.7 mmol) of 1-(4-aminophenyl)-3-methylcarbamoyl-4-methyl-7,8-methylenedioxy-3,4-dihydro-5H-2,3-benzodiazepine (see Example 98) dissolved in 45 ml of anhydrous dichloromethane, the reaction mixture was stirred at 25° C. for 6 days. Then the crystalline precipitate was filtered, washed with 3×2 ml of dichloromethane and dried at 60° to 80° C. to obtain 0.55 g (79.7%) of the pure aimed product, m.p.: 181°–183° C.

$C_{21}H_{23}N_5O_4=409.455$

EXAMPLE 114

1-(4-Aminophenyl)-3-n-butylcarbamoyl-4-methyl-7,8-methylenedioxy-3,4-dihydro-5H-2,3-benzodiazepine It was prepared from 1-(4-nitrophenyl)-3-n-butylcarbamoyl-4-methyl-7,8-methylenedioxy-3,4-dihydro-5H-2,3 benzodiazepine, m.p.: 173°–175° C.

$C_{22}H_{26}N_4O_3=394.482$

The starting substance was prepared as described for the starting substance of Example 98, except that n-butyl isocyanate was used instead of methyl isocyanate and the reaction mixture was stirred for 5 days at 25° C., m.p. 176°–178° C.

$C_{22}H_{24}N_4O_5=424.466$

EXAMPLE 115

1-(4-Glycylaminophenyl)-3-methylcarbamoyl-4-methyl-7,8-methylenedioxy-3,4-dihydro-5H-2,3-benzodiazepine It was prepared from 1-[4-(N-phthaloylglycylamino)-phenyl]-3-methylcarbamoyl-4-methyl-7,8-methylenedioxy-3,4-dihydro-5H-2,3-benzodiazepine by using the process of Example 66 as modified in Example 82, m.p.: 163°–165° C.

$C_{21}H_{23}N_5O_4=409.455$

The starting substance was prepared from 1-(4-aminophenyl)-3-methylcarbamoyl-4-methyl-7,8-methylenedioxy-3,4-dihydro-5H-2,3-benzodiazepine (see Example 98) according to Example 79, m.p. 270°–271° C. (decomp.).

$C_{29}H_{25}N_5O_6=539.559$

EXAMPLE 116

1-(4-Aminophenyl)-3-(N-methylglycyl)-4-methyl-7,8-methylenedioxy-3,4-dihydro-5H-2,3-benzodiazepine 1.03 g (15.3 mmol) of methylamine hydrochloride and 2.64 ml (18.3 mmol) of triethylamine were added to a suspension containing 1.23 g (3.06 mmol) of 1-(4-nitrophenyl)-3-chloroacetyl-4-methyl-7,8-methylenedioxy-3,4-dihydro-5H-2,3-benzodiazepine in 140 ml of ethanol and the reaction mixture was refluxed for 10 hours, then evaporated under reduced pressure. The residue was dissolved in 30 ml of chloroform, washed with 20 ml of 4% NaOH solution, then 2×20 ml of water, dried and evaporated under reduced pressure. The residue was reduced according to the process of Example 16 and the product obtained was purified by column chromatography (adsorbent: Kieselgel 60, eluent: methanol—benzene 4:1). The crude product obtained was triturated with 5 ml of ethyl acetate at 25° C. to obtain 0.60 g (53.6%) of the aimed product, m.p. 198°–200° C. (weak decomp.).

$C_{20}H_{22}N_4O_3=366.428$

The starting compound was obtained from 1-(4-nitrophenyl)-4-methyl-7,8-methylenedioxy-3,4-dihydro-5H-2,3-benzodiazepine (see Example 26) and chloroacetic acid by using the process of Example 33, m.p. 189°–191° C. (decomp.).

$C_{19}H_{16}ClN_3O_5=401.818$

EXAMPLE 117

1-[4-(N-methylglycylamino)phenyl]-3-acetyl-4-methyl-7,8-methylenedioxy-3,4-dihydro-5H-2,3-benzodiazepine 1.31 g (19.5 mmol) of methylamine hydrochloride and 3.24 ml (23.3 mmol) of triethylamine were added to a suspension containing 1.61 g (3.89 mmol) of 1-(4-chloroacetylaminophenyl)-3-acetyl-4-methyl-7,8-methylenedioxy-3,4-dihydro-5H-2,3-benzodiazepine (see Example 106) in 100 ml of ethanol and the reaction mixture was refluxed for 10 hours, then evaporated under reduced pressure. The residue was purified by column chromatography (adsorbent: Kieselgel 60, eluent: chloroform—methanol 9:1). The crude product was triturated with 3 ml of 50% ethanol at 25° C. to give 0.61 g (38.6%) of the aimed product, m.p.: 220°–222° C. (weak decomp.).

$C_{22}H_{24}N_4O_4=408.466$

EXAMPLE 118

Preparation of pharmaceutical compositions

Tablets or divided tablets containing 25 mg of 1-(4-aminophenyl)-3-acetyl-4-methyl-7,8-methylenedioxy-3,4-dihydro-5H-2,3-benzodiazepine (compound of Examples 15 or 16) or 25 mg of 1-(4-acetylaminophenyl )-3-acetyl-4-methyl-7,8-methylenedioxy-3,4-dihydro-5H-2,3-benzodiazepine (compound of Example 42) or 25 mg of 1-(4-aminophenyl)-3-methylcarbamoyl-4-methyl-7,8-methylenedioxy-3,4-dihydro-5H-2,3-benzodiazepine (compound of Example 98) each as active ingredient were prepared by usual methods.

a) Composition of one tablet:

| a) Composition of one tablet: | |
|---|---|
| Active ingredient | 25 mg |
| Potato starch | 43 mg |
| Lactose | 160 mg |
| Polyvinylpyrrolidone | 6 mg |
| Magnesium stearate | 1 mg |
| Talc | 30 mg |
| b) An other preferred composition of one tablet: | |
| Active ingredient | 25 mg |
| Lactose | 130 mg |
| Maize starch | 25 mg |
| Microcrystalline cellulose | 10 mg |

| | |
|---|---|
| Gelatine | 4 mg |
| Talc | 2 mg |
| Stearin | 1 mg |
| Magnesium stearate | 1 mg | e

EXAMPLE 119

(−)-1-(4-Nitrophenyl)-4-methyl-7,8-methylenedioxy-3,4-dihydro-5H-2,3-benzodiazepine Method A A solution of 4.75 g (18.6 mmol) of (S)-(−)-2-amino-3-methyl1,1-diphenylbutan-1-ol in dry methylene chloride (50 ml) was cooled to −70° C. and treated with 9.5 ml (17 mmol) 1.8M solution of borane in THF over a 20 minute period under an atmosphere of dry nitrogen. The resulting solution was gradually warmed to 0° C. and allowed to stand overnight at 4° C. This fixture was treated with a solution of 5.0 g (15.5 mmol) 1-(4-nitrophenyl)-4-methyl-7,8-methylenedioxy-5H-2,3-benzodiazepine in dry methylene chloride (100 ml) at room temperature over a period of about 1 hour. The resulting solution was allowed to stand at room temperature for seven days. The reaction was quenched by the addition of 10% aqueous sodium carbonate (15 ml). The resulting phases were separated and the organic layer washed with water (2×50 ml) each, dried over anhydrous sodium sulfate, and concentrated in vacuo to give a yellow crystalline solid. This solid was suspended in ethanol (50 ml), filtered, and dried to give 4.47 g (88.6% by weight) of the title compound, $[\alpha]_D$=−118° (c=1.0, CHCl$_3$). Proton NMR spectroscopy using a shift reagent (Eu(hfc)$_3$) shows the product as 90:10 mixture of enantiomers. This material was dissolved in hot ethyl acetate (48 ml) and allowed to stand at room temperature overnight. The crystalline precipitate was separated by filtration, washed with ethyl acetate (3×5 ml), and dried to give 2.87 g (56.9% by weight) of the title compound. Proton NMR spectroscopy using a shift reagent (Eu(hfc)$_3$) technique as well as chiral HPLC analysis (CHIRALCEL OJ: mobile phase hexane-isopropanol 35:65) show this material to have an enantiomeric purity of more than 98%. Melting point 171°–172.5° C.

$[\alpha]_D$=−155.6° (c=1.0, CHCl$_3$).

Method B

A solution of 5.0 g (18.6 mmol) of (S)-(−)-2-amino-1,1-diphenyl-4-methylpentan-1-ol in dry dichloroethane (50 ml) was cooled to −10° C. and treated with 1.6 ml (17 mmol) of borane dimethyl sulfide complex over a 20 minute period under an atmosphere of dry nitrogen. The resulting solution was allowed to stand at 4° C. for 15 hours. This mixture was treated with a solution of 5.0 g (15.5 mmol) of 1-(4-nitrophenyl)-4-methyl-7,8-methylenedioxy-5H-2,3-benzodiazepine in dry dichloroethane (100 ml) over a period of about 1 hour at room temperature. The reaction mixture obtained was stirred at 60° C. for 3 hours. Then the reaction was quenched by the addition of 10% aq. sodium carbonate solution (15 ml) and the mixture was stirred for 30 minutes. The organic phase was separated, washed twice with water (2×50 ml) each, dried over anhydrous sodium sulfate and concentrated under reduced pressure. After suspending the crystalline residue in ethanol (50 ml), the orange-yellow crystals were filtered, washed twice with ethanol (2×5 ml) each and dried at 50 to 60° C. to obtain 4.2 g (83.3%) of primary product, $[\alpha]_D$=142.1° (c=1.0, CHCl$_3$), which contained the (−) enantiomer related to the (+) enantiomer in a 93:7 ratio (based on HPLC analysis).

By recrystallizing the primary product from hot ethyl acetate (78 ml), 3.05 g (60.5%) of the title compound were obtained $[\alpha]_D$=−153.6° (c=1.0, CHCl$_3$), melting point 171°–173° C., which contained the minor enantiomer in an amount lower than 1% (based on proton NMR shift reagent technique as well as HPLC analysis).

EXAMPLE 120

(+)-1-(4-Nitrophenyl)-4-methyl-7,8-methylenedioxy-3,4-dihydro-5H-2,3-benzodiazepine Method A The title compound was prepared as described in Method A of Example 119 using (R)-(+)-2-amino-3-methyl-1,1-diphenylbutan-1-ol.

Melting point 172°–174° C.

$[\alpha]_D$=+153.40° (c=1.0, CHCl$_3$)

Enantiomeric purity: >98%

Method B

Method B of Example 119 was followed by starting from 5.0 g (18.6 mmol) of (R)-(+)-2-amino-1,1-diphenyl-4-methylpentan-1-ol to give 4.17 g (82.7%) of primary product, $[\alpha]_D$=+140.6° (c=1.0, CHCl$_3$), which contained the (+) enantiomer related to the (−) enantiomer in a 93:7 ratio (based on HPLC analysis).

By recrystallizing the primary product from hot ethyl acetate (75 ml), 3.07 g (60.8%) of the title compound were obtained, $[\alpha]_D$=+155.2° (c=1.0, CHCl$_3$), melting point 172°–174° C., which contained the minor enantiomer in an amount lower than 1% (based on proton NMR shift reagent technique as well as HPLC analysis).

EXAMPLE 121

(−)-1-(4-Nitrophenyl)-3-methylcarbamoyl-4-methyl-7,8-methylenedioxy-3,4-dihydro-5H-2,3-benzodiazepine A solution of the compound prepared as described in Method A or Method B of Example 119 (4.0 g) in dry methylene chloride (80 ml) was treated with methylisocyanate (2.18 ml). The resulting reaction mixture was stirred at room temperature for three days. This reaction mixture was evaporated in vacuo and the oily residue treated with water (60 ml). The resulting precipitate was filtered and dried to give 4.49 g of the title compound which was a yellow powder. This material was used in the next step without further purification.

$[\alpha]_D$=−315.3° (c=1.0, CHCl$_3$)

EXAMPLE 122

(+)-1-(4-Nitrophenyl)-3-methylcarbamoyl-4 methyl-7,8-methylenedioxy-3,4-dihydro-5H-2,3 benzodiazepine The title compound was prepared from the compound of Example 120 using the process described in Example 121.

$[\alpha]_D$=+304.09° (c=1, CHCl$_3$)

EXAMPLE 123

(−)-1-(4-Aminophenyl)-3-methylcarbamoyl-4-methyl-7,8-methylenedioxy-3,4-dihydro-5H-2,3 benzodiazepine A suspension of the compound prepared as described in Example 122 (2.42 g) and Raney nickel (W-2, 0.5 g) in methanol (50 ml) was treated with 98% hydrazine hydrate (1.1 ml). After stirring the reaction mixture for 1 hour at 25° C., the catalyst was removed by filtration, and the filtrate was evaporated in vacuo. The oily residue was treated with water (50 ml). The resulting precipitate was filtered and dried to give 2.06 g of the crude solid. This material was dissolved in ethanol (10 ml) and concentrated to a small volume in vacuo. The residue was treated with benzene (26 ml) to induce crystallization. The crystalline product was collected by filtration, and dried at reduced pressure (36 hrs., 100° C., 80 torr), to give 1.98 g of the title compound as a light yellow powder. Melting point 133°–135° C.

$[\alpha]_D = -376.65°$ (c=1, CHCl$_3$)

Enantiomeric purity: >99%

EXAMPLE 124

(+)-1-(4-Aminophenyl)-3-methylcarbamoyl-4-methyl-7,8-methylenedioxy-3,4-dihydro-5H-2,3 benzodiazepine The title compound was prepared from the compound of Example 121 using the process described in Example 123.

Melting point 133°–135° C.

$[\alpha]_D = +363.4°$ (c=1, CHCl$_3$)

Enantiomeric purity: >99%

EXAMPLE 125

(−)-1-(4-Nitrophenyl)-3-acetyl-4-methyl-7,8-methylenedioxy-3,4-dihydro-5H-2,3-benzodiazepine A mixture of the compound prepared as described in Method A or Method B of Example 119 (2.34 g) and acetic anhydride (11.7 ml) was stirred at room temperature. After 15 minutes, dissolution of the benzodiazepine was complete. After 2 hours, the reaction mixture was cooled in an ice-water bath and treated with water (60 ml). After stirring overnight, the crystalline product was collected, washed with water (4×5 ml), and dried to give 2.5 g of the title compound as pale yellow crystals. Melting point 173°–177° C.

$[\alpha]_D = -54.9°$ (c=1, CHCl$_3$)

EXAMPLE 126

(+)-1-(4-Nitrophenyl)-3-acetyl-4-methyl-7,8-methylenedioxy-3,4-dihydro-5H-2,3-benzodiazepine The title compound was prepared from the compound of Example 120 using the process described in Example 125.

Melting point 173°–177° C.

$[\alpha]_D = +49.6°$ (c=1, CHCl$_3$)

EXAMPLE 127

(+)-1-(4-Aminophenyl)-3-acetyl-4-methyl-7,8-methylenedioxy-3,4-dihydro-5H-2,3-benzodiazepine A suspension of the compound prepared as described in Example 125 (2.6 g) and Raney nickel (W-2, 0.5 g) in methanol (52 ml) was treated with 98% hydrazine hydrate (1.2 ml). After stirring the reaction mixture for 1 hour at room temperature, the catalyst was removed by filtration, and the filtrate evaporated in vacuo. The oil residue was treated with water (50 ml). The resulting precipitate was filtered and dried to give 2.17 g of the crude solid. This material was recrystallized from ethyl acetate (39 ml), the crystalline product collected and dried (36 hrs, 120°–130° C., 80 torr) to give 1.8 g of the title compound. Melting 169°–171.5° C.

$[\alpha]_D = +313.41°$ (c=1, MeOH)

Enantiomeric purity: >99%

EXAMPLE 128

(−)-1-(4-Aminophenyl)-3-acetyl-4-methyl-7,8-methylenedioxy-3,4-dihydro-5H-2,3-benzodiazepine The title compound was prepared from the, compound of Example 126 using the process described in Example 127.

Melting point 169°–172° C.

$[\alpha]_D = -321.34°$ (c=1, MeOH)

Enantiomeric purity: >99%

We claim:

1. A method of treating acute and chronic neurodegenerative disorders in mammals, which comprises administering to a mammal in need of such treatment a pharmaceutically effective amount of a compound of formula (I)

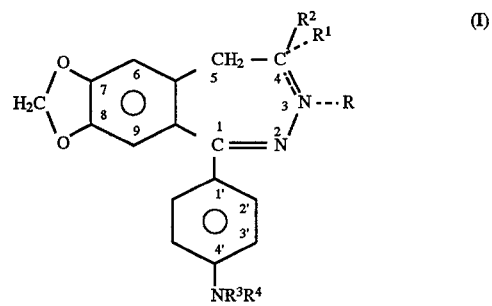

wherein

R is a $C_{1-6}$ alkanoyl group optionally substituted by a methoxy, cyano, carboxyl, amino, $C_{1-4}$alkylamino, di($C_{1-4}$alkyl)amino, pyrrolidino, phthalimido or phenyl group, or by one or more halogen(s); or R is a benzoyl, cyclopropanecarbonyl, $C_{1-5}$alkylcarbamoyl or phenylcarbamoyl group; or R is absent when a double bond exists between the N(3) and C(4) atoms;

$R^1$ is hydrogen, or $R^1$ is absent when a double bond exists between the N(3) and C(4) atoms;

$R^2$ is a $C_{1-3}$alkyl group; or $R^1$ and $R^2$ together form a methylene group;

$R^3$ is hydrogen or a $C_{1-4}$ alkanoyl group;

$R^4$ is hydrogen; a $C_{1-6}$ alkanol group optionally substituted by a methoxy, cyano, carboxyl, amino, $C_{1-6}$alkylamino, di($C_{1-4}$alkyl)amino, pyrrolidino, phthalimido or phenyl group or by one or more halogen (s); as well as a benzoyl, palmitoyl, cyclopropanecarbonyl, $C_{1-5}$alkylcarbamoyl or phenylcarbamoyl group; with the proviso that no double bond exists between the N(3) and C(4) atoms when both $R^3$ and $R^4$ stand for hydrogen; and stereoisomers and pharmaceutically acceptable acid-addition salts of said compound.

2. The method of claim 1, wherein the compound administered is a compound selected from the group consisting of 1-(4-aminophenyl)-3-acetyl-4-methyl-7,8-methylenedioxy-3,4-dihydro-5H-2,3-benzodiazepine, 1-(4-aminophenyl)-3-propionyl-4-methyl-7,8-methylenedioxy-3,4-dihydro-5H-2,3-benzodiazepine, 1-(4-acetylaminophenyl)-3-acetyl-4-methyl-7,8-methylenedioxy-3,4-dihydro-5H-2,3-benzodiazepine, 1-(4-propionylaminophenyl)-3-propionyl- 4-methyl-7,8-methylenedioxy-3,4-dihydro-5H-2,3-benzodiazepine, 1-(4-propionylaminophenyl)-3-acetyl-4-methyl-7,8-methylenedioxy-3,4-dihydro-5H-2,3-benzodiazepine, 1-(4-acetylaminophenyl)-3-propionyl-4-methyl-7,8-methylenedioxy-3,4-dihydro-5H-2,3-benzodiazepine, 1-(4-propionylaminophenyl)-3-formyl-4-methyl-7,8-methylenedioxy-3,4-dihydro-5H-2,3-benzodiazepine, 1-(4-trifluoroacetylaminophenyl)-3-acetyl-4-methyl-7,8-methylenedioxy-3,4-dihydro-5H-2,3-benzodiazepine, 1-(4-glycylaminophenyl)-3-acetyl-4-methyl-7,8-methylenedioxy-3,4-dihydro-5H-2,3-benzodiazepine, $N^1$-(4-(3-acetyl-4-methyl-7,8-methylenedioxy-3,4-dihydro-5H-2,3-benzodiazepine-1-yl)-phenyl)-$N^3$-methylurea, 1-(4-(N,N-dimethylglycylamino)phenyl)-3-acetyl-4-methyl-7,8-methylenedioxy-3,4-dihydro-5H-2,3-benzodiazepine, 1-(4-(N,N-diethylglycylamino)phenyl)-3-acetyl-4-methyl-7,8-methylenedioxy-3,4-dihydro-5H-2,3-benzodiazepine, 1-(4-(1-pyrrolidinoacetylamino)phenyl)-3-acetyl-4-methyl-7,8-methylenedioxy-3,4-dihydro-5H-2,3-benzodiazepine and 1-(4-glycylaminophenyl)-3-methylcarbamoyl-4-methyl-7,8-methylenedioxy-3,4-dihydro-5H-2,3-benzodiazepine and pharmaceutically acceptable acid-addition salts thereof.

3. The method of claim 1, wherein a compound selected from the group consisting of (−)-1-(4-aminophenyl)-3-acetyl-4-methyl-7,8-methylenedioxy-3,4-dihydro-5H-2,3-benzodiazepine and (−)-1-(4-aminophenyl)-3-methylcarbamoyl-4-methyl-7,8-methylenedioxy-3,4-dihydro-5H-2,3-benzodiazepine is administered.

4. The method of claim 1, wherein the disorder treated is cerebral ischaemia.

5. The method of claim 2, wherein the disorder treated is cerebral ischaemia.

6. The method of claim 3, wherein the disorder treated is cerebral ischaemia.

* * * * *